United States Patent
Angelescu et al.

(10) Patent No.: US 8,950,246 B2
(45) Date of Patent: Feb. 10, 2015

(54) THERMAL BUBBLE POINT MEASUREMENT SYSTEM AND METHOD

(75) Inventors: Dan Angelescu, Noisy le Grand Cedex (FR); Matthew Sullivan, Cambridge, MA (US); Edward Harrigan, Richmond, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 1094 days.

(21) Appl. No.: 12/810,033

(22) PCT Filed: Dec. 19, 2008

(86) PCT No.: PCT/US2008/087573
§ 371 (c)(1),
(2), (4) Date: Nov. 10, 2010

(87) PCT Pub. No.: WO2009/082674
PCT Pub. Date: Jul. 2, 2009

(65) Prior Publication Data
US 2011/0259090 A1  Oct. 27, 2011

Related U.S. Application Data

(60) Provisional application No. 61/016,457, filed on Dec. 22, 2007.

(51) Int. Cl.
*G01N 1/00* (2006.01)
*G01N 33/28* (2006.01)

(52) U.S. Cl.
CPC .................................. *G01N 33/2823* (2013.01)
USPC ........................................................ 73/64.56

(58) Field of Classification Search
USPC ......................................................... 73/64.56
See application file for complete search history.

(56) References Cited

U.S. PATENT DOCUMENTS

| | | | | |
|---|---|---|---|---|
| 3,891,826 A | * | 6/1975 | Seuthe et al. | 392/405 |
| 4,007,785 A | * | 2/1977 | Allen et al. | 166/272.1 |
| 4,116,045 A | * | 9/1978 | Potter | 73/61.46 |
| 4,251,809 A | * | 2/1981 | Cheney | 340/603 |
| 4,782,695 A | * | 11/1988 | Glotin et al. | 73/152.51 |
| 5,014,553 A | * | 5/1991 | Hori et al. | 73/295 |
| 5,329,811 A | * | 7/1994 | Schultz et al. | 73/152.02 |

(Continued)

FOREIGN PATENT DOCUMENTS

DE   2514584 A   * 12/1976

OTHER PUBLICATIONS

N. W. Bostrom, et al., "Ultrasonic bubble point sensor for petroleum fluids in remote and hostile environments," Measurement. Science and Technology. 16, p. 2336, 2005.

(Continued)

*Primary Examiner* — John Fitzgerald
(74) *Attorney, Agent, or Firm* — Darryl R. Wright; Jody DeStefanis

(57) ABSTRACT

A method and an apparatus for nucleating bubbles in an oil-gas mixture, including introducing a sample comprising an oil-gas mixture into a chamber; and heating the sample with a heater until at least one bubble is thermally nucleated in the chamber. The bubble point (BP) pressure of the sample can be determined by detecting pressure at two points in a system, which includes the chamber and the heater, and by determining the behavior of the nucleated bubble as the pressure on the bubble is varied.

28 Claims, 17 Drawing Sheets

(56) References Cited

U.S. PATENT DOCUMENTS

| | | | |
|---|---|---|---|
| 6,490,916 B1 | 12/2002 | Schlumberger | |
| 6,758,090 B2 | 7/2004 | Schlumberger | |
| 6,875,619 B2 | 4/2005 | Blackburn | |
| 6,929,134 B2* | 8/2005 | Fujita | 219/388 |
| 7,458,257 B2* | 12/2008 | Pop et al. | 73/152.04 |
| 7,556,096 B2* | 7/2009 | Vinegar et al. | 166/250.01 |
| 7,752,906 B2* | 7/2010 | Pop et al. | 73/152.04 |
| 8,056,408 B2* | 11/2011 | Pop et al. | 73/152.04 |
| 2002/0194907 A1* | 12/2002 | Bostrom et al. | 73/152.58 |
| 2004/0252748 A1* | 12/2004 | Gleitman | 374/130 |
| 2005/0117894 A1* | 6/2005 | Khoury | 392/313 |
| 2006/0117962 A1* | 6/2006 | Hoekstra et al. | 99/403 |
| 2006/0186112 A1* | 8/2006 | Valiyambath Krishnan et al. | 219/492 |
| 2006/0233217 A1* | 10/2006 | Gleitman | 374/131 |
| 2007/0061093 A1 | 3/2007 | Angelescu et al. | |
| 2007/0137293 A1* | 6/2007 | Pop et al. | 73/152.23 |
| 2008/0137711 A1* | 6/2008 | Gleitman | 374/161 |
| 2009/0049889 A1* | 2/2009 | Pop et al. | 73/19.09 |

OTHER PUBLICATIONS

S.C. Wilmot, "Techniques to Improve the Quality of Wireline Oil Samples in Wells Drilled With Oil Base Mud," SPWLA 21st Annual Logging Symposium, Jun. 2000.

Betancourt, et al., "Analyzing Hydrocarbons in the Borehole," Oilfield Review, pp. 54-61, Autumn, 2003.

Johanna Levelt Sengers, "How Fluids Unmix: Discoveries by the School of Van der Waals and Kamerlingh Onnes," Royal Netherlands Academy of Arts and Sciences, 2002.

* cited by examiner

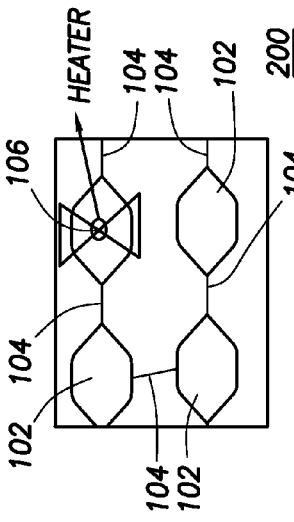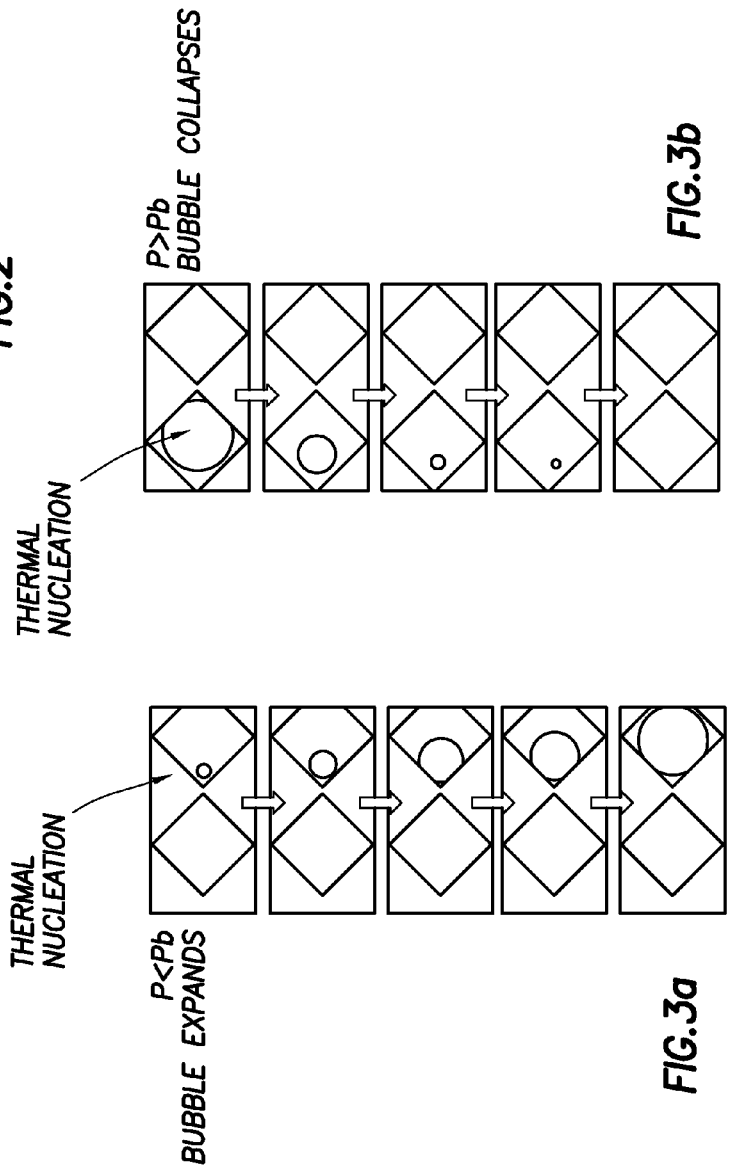

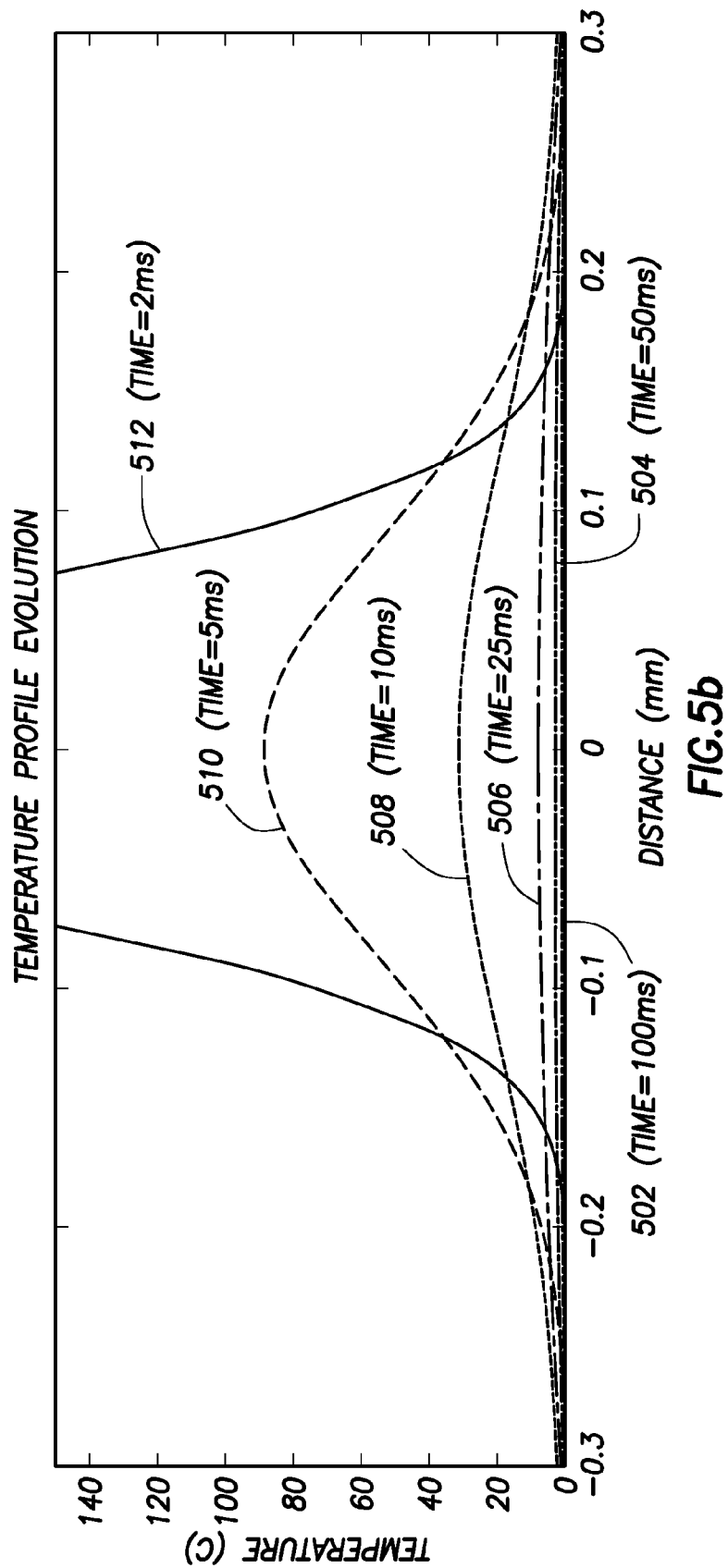

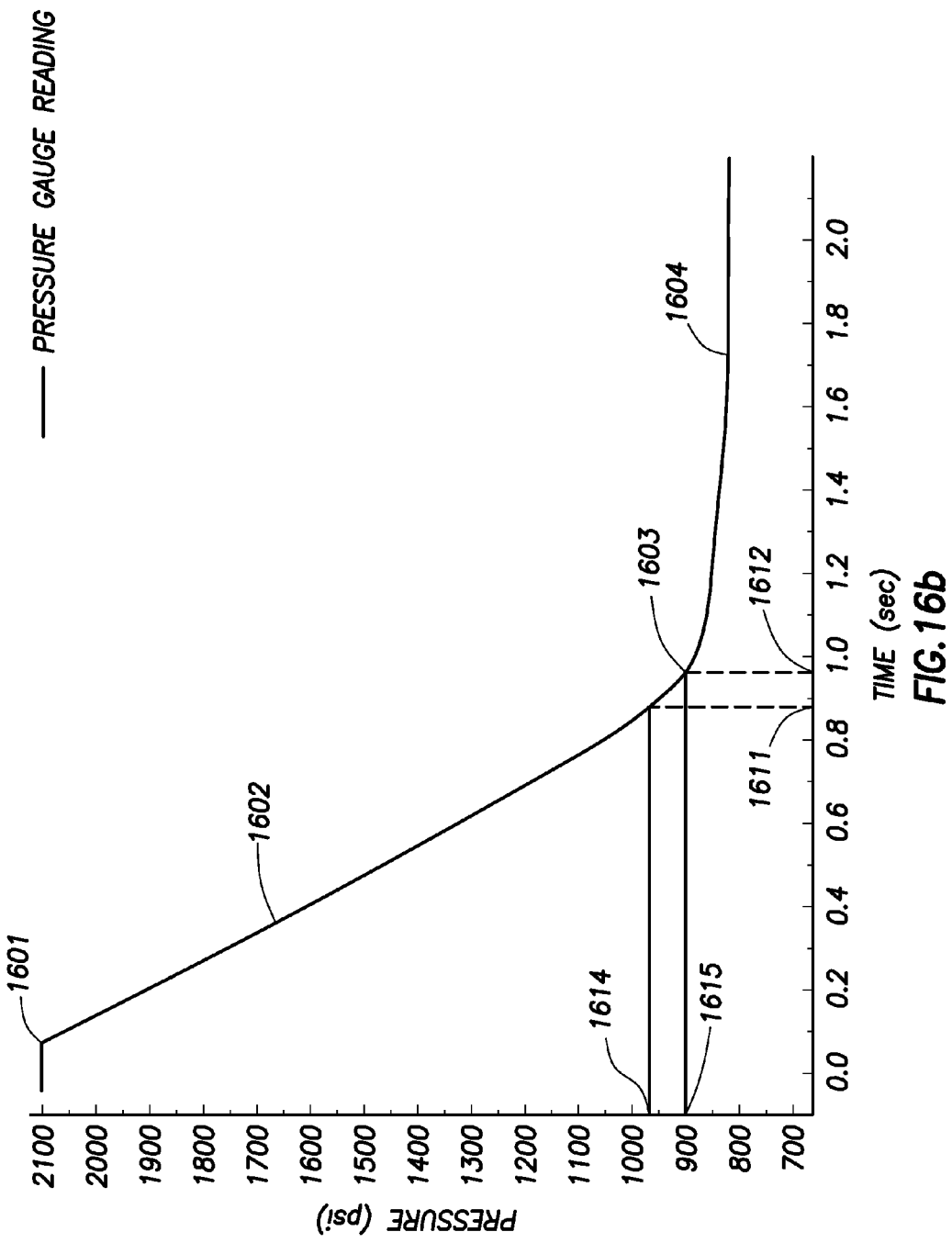

THERMAL BUBBLE POINT MEASUREMENT SYSTEM AND METHOD

CROSS REFERENCE TO RELATED DOCUMENTS

The present invention claims benefit of priority to U.S. Provisional Patent Application Ser. No. 61/016,457 of Dan ANGELESCU et al., entitled "THERMAL BUBBLE POINT MEASUREMENT SYSTEM AND METHOD," filed on Dec. 22, 2007, the entire content of which is hereby incorporated by reference herein.

BACKGROUND OF THE INVENTION

1. Field of the Invention

The present invention generally relates to fluid analysis, and more particularly to a thermal bubble point measurement system and method.

2. Discussion of the Background

Fluid analysis is of utmost importance to the oilfield industry. Production decisions for a new well are largely based on measurements of fluid properties, either performed downhole (e.g., directly on the reservoir fluids) or in the lab (e.g., on a sample acquired downhole). Information regarding the chemical composition, phase diagram (e.g., including information on the amount of dissolved gas), density and viscosity of an oil, is critical to deciding which zones of a particular well are economical to produce, and to planning the right infrastructure for production.

One particular issue of concern is the bubble point (BP) pressure of the oil. At high pressures and temperatures similar to those prevalent downhole, a significant amount of gas (e.g., carbon dioxide and the light hydrocarbons, such as methane, ethane, propane, butane and pentane) can be dissolved in the oil phase. The pressure of the oil typically drops during the production process, which may cause the dissolved gas to segregate into a separate gas phase. This process needs to be performed in a very controlled environment, as hydrocarbon gas is highly flammable and compressible, which can lead to major blow-outs and explosions at a well site. Additionally, the permeability of a gas-oil mixture through a porous rock can be reduced by several orders of magnitude by the presence of bubbles, making production impossible. In order to limit the risks of a blow-out and of permeability reduction due to bubble formation, limitations need to be placed on production rates, and the well must often be pressurized at pressures comparable to or even higher than the BP pressure to limit the amount of gas going out of solution.

It is evidently crucial to understand the phase properties of formation oils, particularly the BP pressure at the prevalent temperature in the well. Currently, such phase analysis is performed in several labs around the world, but usually on samples collected downhole, brought to the surface and often stored for a long time prior to analysis (e.g., as described in N. W. Bostrom, D. D. Griffin, R. L. Kleinberg and K. K. Liang, "Ultrasonic bubble point sensor for petroleum fluids in remote and hostile environments," Meas. Sci. Technol. 16, p. 2336, 2005). Many techniques exist to detect the bubble point in a laboratory environment. Best current lab practice relies on slow depressurization of the sample, while agitating the fluid with an impeller. Optical detection is typically used for bubble identification. Alternatively, the pressure-volume characteristics of the sample can be monitored to detect the considerable change in compressibility at bubble point (e.g., as described in Bostrom et al. cited above). Preliminary work on implementing phase-separation tests in downhole tools has been performed by Esso (e.g., as described in S. C. Wilmot: "Techniques To Improve The Quality Of Wireline Oil Samples In Wells Drilled With Oil Base Mud", SPWLA 21st Annual Logging Symposium, June 2000) in order to ascertain oil base mud filtrate contamination of the hydrocarbon sample.

The present invention includes the recognition that sample treatment in phase analysis as is performed in several labs around the world, wherein samples are collected downhole, brought to the surface and often stored for a long time prior to analysis (e.g., as described in Bostrom et al. cited above), is likely to trigger irreversible changes in the composition and phase behavior of the fluid (e.g., asphaltene and wax precipitation), making subsequent measurements of BP pressure less accurate. Accordingly, there is a very strong need for developing a bubble point measurement scheme that could be deployed downhole, making sample acquisition obsolete. Physical size of such a device is important, since integration in a downhole tool imposes stringent limitations on the real estate available. The simplest imaginable measurement to detect the BP pressure includes depressurizing a sample of oil in a controlled manner, while monitoring its content for appearance of bubbles. However, such a measurement can introduce major errors in the determination of bubble point pressure, due to the likely condition of supersaturation. In a supersaturated fluid, a bubble may not form spontaneously despite an ambient pressure lower than the bubble point pressure. To avoid errors due to supersaturation, there is a need for a reliable way of nucleating bubbles. One way of nucleating bubbles is mentioned in the work cited above of Bostrom et al., demonstrating the use of an ultrasonic transducer to both nucleate bubbles by means of cavitation near the bubble point pressure and detect persistent bubbles; however, such method involves significant sample volumes, and because the nucleation occurs in the bulk of the fluid, the exact position of the nucleated bubbles cannot be controlled.

Therefore, there is a need for a method and apparatus (e.g., which also can be referred to herein as a "system") that addresses the above problems of existing systems, although other problems with existing systems will be apparent from the entire description herein. The above and other needs and problems are addressed by the exemplary embodiments of the present invention.

SUMMARY OF THE INVENTION

The present invention provides a method and apparatus for nucleating bubbles in and measuring BP pressure of an oil-gas mixture. Advantageously, the present invention provides controlled bubble nucleation and detection by providing means to define (or e.g., control) the time and the place of nucleation. Such features, when (in some embodiments) coupled with confinement provided by a micro-fluidic environment, allow very accurate measurements to be performed on a bubble subsequent to nucleation, which in turn can lead to improved bubble point measurements.

Accordingly, in exemplary aspects of the present invention there is provided a method for nucleating bubbles in an oil-gas mixture, including introducing a sample comprising an oil-gas mixture into a chamber; and heating the sample with a heater until at least one bubble is thermally nucleated in the chamber. The method may further include the determination of the bubble point (BP) pressure of the sample by detecting pressure at two points in a system or device that may include a plurality of chambers, which can be interconnected in a suitable manner, e.g., by a plurality of capillaries. The pressure can be detected, e.g., by using at least two sensors. The BP pressure can be determined from a phase diagram for the oil-gas mixture. In one exemplary aspect of the present invention, the presence of a micro-heater is accompanied by that of a microscopic bubble detector, placed in immediate vicinity of, or coincidental with, the micro-heater, to detect the presence and monitor the behavior of a bubble that has been nucleated by thermal means.

In another embodiment, an apparatus or system is provided for nucleating bubbles in an oil-gas mixture, which includes a chamber configured to receive a sample comprising an oil-gas mixture and a heater configured to heat the sample until at least one bubble is thermally nucleated in the chamber. The apparatus or system may further include a means for determining the BP pressure of the sample, which comprises at least two sensors placed at two distinct points of the system or device. The BP pressure can be determined from the phase behavior of the sample. In one exemplary aspect of the invention an apparatus is provided that incorporates a microscopic bubble detector, coinciding with, or in close proximity of a micro-heater, to detect the presence and monitor the behavior of a bubble that has been nucleated by thermal means.

In another aspect, the present invention provides a micro-fluidic apparatus for nucleating bubbles in an oil-gas mixture, the micro-fluidic apparatus comprising: a micro-chamber configured to receive a sample comprising an oil-gas mixture; a micro-heater configured to heat the sample until at least one bubble is thermally nucleated in the micro-chamber; a capillary in fluid communication with the micro-chamber, the capillary having an inlet for introducing the sample into the micro-chamber, and an outlet; and detection means for detecting the at least one nucleated bubble and monitoring the behavior thereof. The detection means may include using a thermal technique, or optically monitoring a behavior of the nucleated bubble. Where the detection means includes a thermal technique, such thermal technique may include using the micro-heater as a thermal conductivity detector after the thermal nucleation of the bubble. However, the thermal technique may use a thermal conductivity detector that is separate from the micro-heater, and physically located in a path of travel of the bubble nucleated at the heater. Furthermore, the micro-chamber and micro-heater may be among a plurality of micro-chambers interconnected by a plurality of capillaries.

The micro-fluidic apparatus may further comprise means for determining the BP pressure of the sample. Such means for determining the BP pressure of the sample may comprise at least two sensors placed at two distinct points of the micro-fluidic apparatus. In addition, such means for determining the BP pressure of the sample may be configured to measure BP pressure of the sample downhole or on surface. The micro-fluidic apparatus may further comprise external means for modifying pressure of the sample operably connected to the micro-chamber. It should be noted that wherein the micro-fluidic apparatus heats the sample until at least one bubble is thermally nucleated in the micro-chamber, such heating may have a minimal affect on the average temperature of the sample.

In the system, apparatus, device or method, some or all components may be micro-fabricated. Thus, the system or device may be a micro-fluidic system or device, the chamber a micro-chamber, the heater a micro-heater and the tubes capillaries.

Still other aspects, features, and advantages of the present invention are readily apparent from the entire description thereof, including the figures, which illustrates a number of exemplary embodiments and implementations. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIG. 1 illustrates an exemplary sensor for thermal bubble point measurement;

FIG. 2 illustrates an exemplary sensor array for thermal bubble point measurement;

FIGS. 3a-3b illustrate exemplary fast camera microscopy of bubble behavior;

FIGS. 5a-5b illustrate exemplary graphs of dependence of temperature on time within a central part of a cavity;

FIGS. 16a-16b illustrate data from the exemplary bubble point measurement system of FIG. 15.

DETAILED DESCRIPTION

Figure 4:
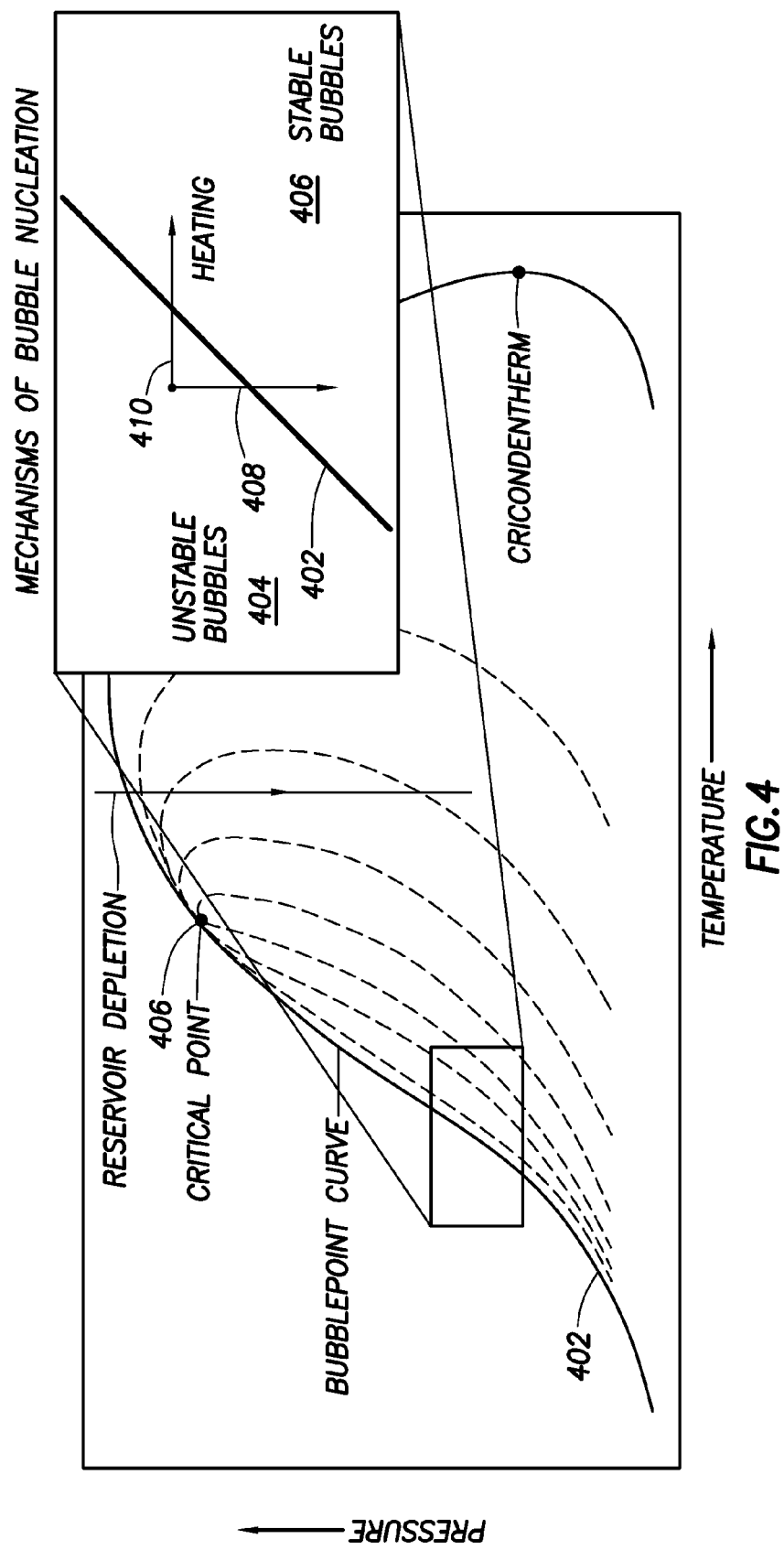
FIG. 4 illustrates an exemplary phase diagram of a typical crude oil.

Various embodiments and aspects of the invention will now be described in detail with reference to the accompanying figures. Still other aspects, features, and advantages of the present invention are readily apparent from the entire description thereof, including the figures, which illustrates a number of exemplary embodiments and implementations. The invention is also capable of other and different embodiments, and its several details can be modified in various respects, all without departing from the spirit and scope of the present invention. Accordingly, the drawings and descriptions are to be regarded as illustrative in nature, and not as restrictive. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Generally, the exemplary embodiments are directed to a method and apparatus for nucleating at least one bubble, detection of the bubble(s) and BP pressure measurement system and method based on thermal nucleation and detection of bubbles, advantageously, which can be performed in bulk fluid or within a micro-fluidic sensor. As noted above, the simplest imaginable measurement to detect the BP pressure includes depressurizing a sample of oil in a controlled manner, while monitoring its content for appearance of bubbles. Such a measurement can however introduce major errors in the determination of bubble point pressure, due to the condition of supersaturation. In a supersaturated fluid a bubble may not form despite an ambient pressure lower than the bubble point pressure. To avoid errors due to supersaturation, a more reliable way of nucleating bubbles should be devised. Any sensor aimed at determining accurately the BP pressure must thus have the means of nucleating a bubble, by means of an impeller or ultrasonic actuator (e.g., mechanical techniques leading to cavitation in the oil), or thermally, as within the scope of the exemplary embodiments.

In one embodiment the sample of oil-gas mixture, placed in a reservoir (e.g., also referred to herein as a "chamber"), is heated with a suitable heater to nucleate at least one bubble in the sample. In any embodiment of the invention, the heater used can be any heater known in the art suitable for a particular environment, such as heaters having metallic heating filaments, such as those made of tungsten commonly used in lighting, which offer the benefit of being thin. Tungsten filaments on the order of a few micrometers in diameter are easily obtainable and exhibit the desired combination of low thermal capacity, rapid thermal response, high sensitivity to changes in temperature and outstanding robustness. One skilled in the art will recognize that alternative filaments can be employed in practicing the present invention, including but not limited to other types of miniaturized metallic wire, such as nickel-chrome heating wire, to fibers coated with thin conductive films, to thin metallic film heaters applied to the surface of a part or of a substrate, or to micro-fabricated silicon filaments. As a variety of heater materials exist, the material of the heater can be tailored to the specific operational environment such that measurements are optimized for an anticipated fluid composition which may necessitate addressing issues such as corrosion and abrasion.

In the context of the present invention, micro-fabrication can include any suitable process capable to produce structures or features that are smaller than approximately 1 millimeter in size. These processes are known to one skilled in the art, and may include without limitation a variety of techniques, such as high-speed machining, diamond turning, electrical discharge machining, laser ablation machining, photolithography, thin-film depositions, dry and wet etching techniques, and any other suitable processes. A micro-fluidic system can include a system having fluid passages that are smaller than approximately one millimeter in size, but larger than approximately 100 nanometers. A micro-chamber can include a cavity that has lateral dimensions that are smaller than approximately one millimeter in size, but larger than approximately 100 nanometers. A micro-heater can include a heater that has dimensions that are smaller than approximately one millimeter in size, but larger than approximately 100 nanometers. A capillary, manufactured using micro-fabrication techniques, preferably has dimensions that are smaller than approximately one millimeter in size, but larger than approximately 100 nanometers. A capillary may also be used which is smaller than approximately one millimeter in size, but not micro-fabricated and instead fabricated using conventional techniques known in the art. For example, a capillary used to connect various components in the micro-fluidic system (e.g., the piston and the micro-fluidic chip). As such, the term "capillary" or "capillary tube" as used herein may refer to a capillary which has been micro-fabricated, and also a capillary which has not been micro-fabricated.

Some exemplary embodiments describe devices capable of nucleating micro-bubbles thermally (e.g., by using miniaturized heaters) and then detecting them by one of several means, as further described. Depending on the fluid pressure relative to bubble point pressure, the nucleated bubble will collapse (e.g., if fluid pressure is above the bubble point pressure) or expand (e.g., if fluid pressure is below the bubble point pressure). By checking whether the nucleated bubble is present at a later time, one can determine whether BP pressure is below or above current fluid pressure. The detection of the bubble can be performed in several distinct ways, depending on which property of the fluid is being measured to discriminate between liquid and gas. For example, the detection of the bubble can be accomplished thermally, using micro-fabricated heaters as transducers to perform a measurement of thermal conductivity, which is significantly lower in a gas than in a liquid (e.g., water or oil). Alternatively, one can detect the presence of a bubble by measuring other properties of the fluid that differ between liquid and gas, such as the dielectric constant (e.g., measured with a capacitive sensor), the density or viscosity (e.g., measured with physical oscillator sensors), the optical density or index of refraction (e.g., measured optically), and the like. One advantage of the exemplary systems and methods of this invention, as compared to previous bubble point measurements is that they allow a controlled generation of bubbles and their immediate monitoring in situ.

To perform an accurate bubble point pressure measurement, in addition to being able to create and detect bubbles, one must provide means of reducing the pressure in a controlled way from borehole pressure down to below bubble point pressure. A sensor used for the detection of the bubble can then detect whether the nucleated bubbles collapse or expand, and hence can detect the transition through the bubble point pressure. When BP pressure is crossed, the behavior of the created bubbles changes from collapsing to expanding, and BP pressure is thus detected or interpolated from available data, such as at least two pressure points, measured along the pressure gradient from the borehole pressure to below the BP pressure. The exemplary embodiments include a way to provide such a controlled pressure gradient in a micro-fluidic system by employing viscous drag through a capillary or series of capillaries. An array of micro-chambers can be fabricated on a substrate, with a series of capillaries connecting subsequent chambers in the array. Fluid at borehole pressure is present at one end of the array, the other end being exposed to a pressure significantly lower than BP pressure (e.g., which could be a vacuum reservoir). The resulting pressure difference between the inlet and outlet of the device creates flow. The pressure within each chamber is quasi uniform (e.g., due to the relatively large size of the chamber relative to the capillary), and slightly lower than the pressure in the previous chamber, resulting in a set of discrete pressure steps. A heater and detector combination can be incorporated in each chamber to determine the position of the local pressure relative to bubble point pressure, and hence provide a measurement of the BP pressure.

Alternatively, pressure can be reduced or modified by using, for example, an externally actuated and controlled piston, diaphragm or system of bellows, and the like, to increase, in a controlled way, the volume of a sample trapped within the BP measurement device. By increasing the volume of the sample at a given temperature, the pressure of the sample decreases. A heater and detector combination, as described above, can be incorporated within the device to nucleate bubbles and monitor the behavior of the nucleated bubbles, such as to determine the position of the current sample pressure relative to the BP pressure.

Referring now to the drawings, wherein like reference numerals designate identical or corresponding parts throughout the several views, and more particularly to FIG. 1 thereof, there is illustrated an exemplary sensor 100 for thermal bubble point measurement, according to one embodiment of the present invention. In FIG. 1, an optical interferometer micrograph of the sensor 100 is shown, having the noted exemplary physical dimensions, and including an illustration of a portion of micro-fabricated chamber 102 (e.g., also referred to herein as "micro-chamber" or "micro-cavity"), and a connecting capillary 104 leading to a next chamber.

FIG. 2 illustrates a larger scale view micrograph of a prototype sensor array 200, including several chambers 102 connected by capillaries 104 and a heater (or e.g., "micro-heater") 106 that acts as a transducer, for creating and detecting bubbles. FIGS. 3a and 3b are fast camera microscopy of a bubble behavior, as a function of sample (e.g., fluid) pressure (P) versus BP pressure (Pb) for P<Pb (FIG. 3a) and P>Pb (FIG. 3b) cases. The nucleated bubble is seen to expand in the first case when the sample pressure is lower than BP pressure and to collapse in the second case when the sample pressure is higher than the BP pressure.

Figure 6:
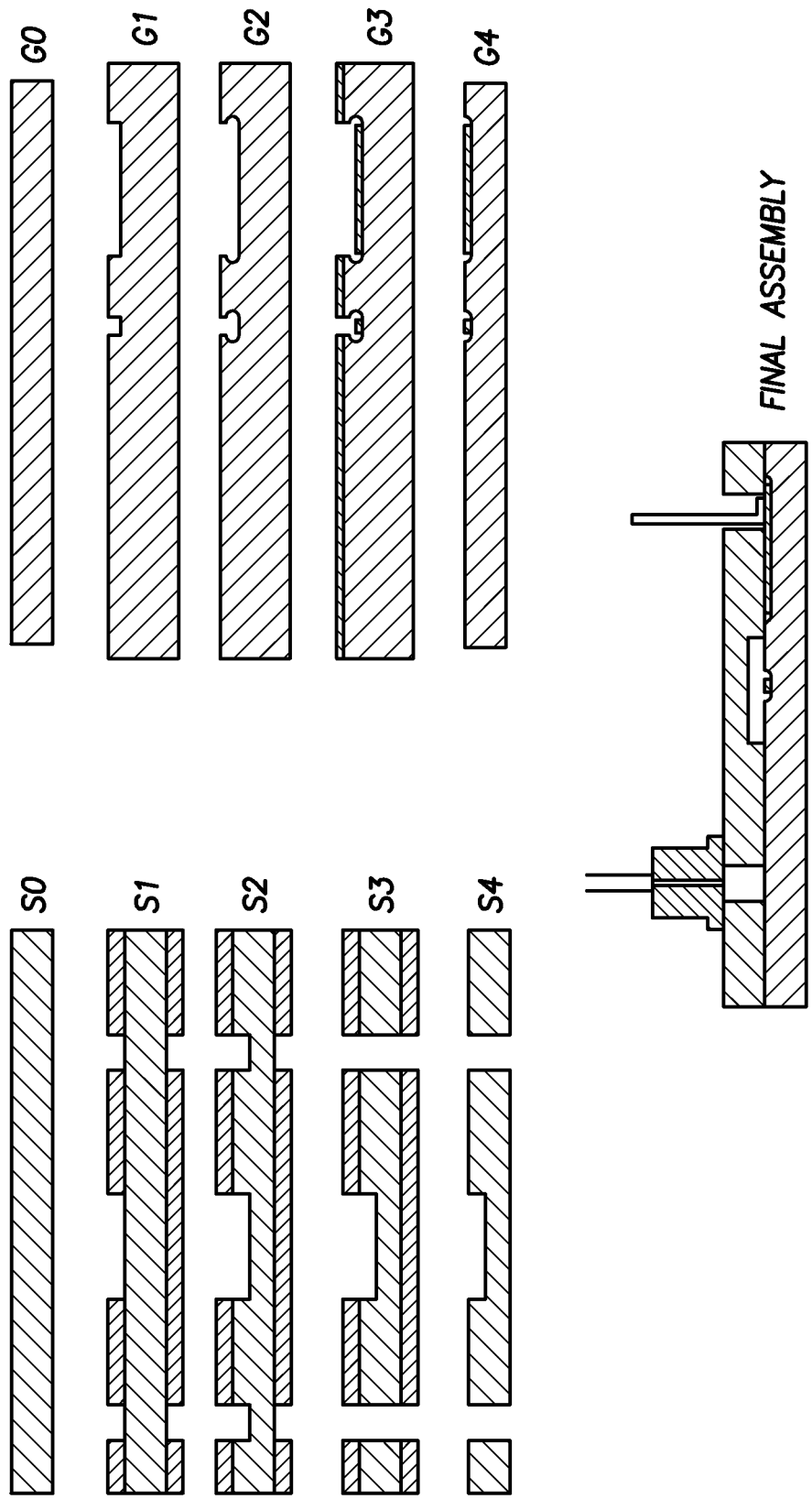
FIG. 6 illustrates an exemplary fabrication of the exemplary bubble-point sensor of FIGS. 1-3.

In FIGS. 1-3, the exemplary device is illustrated, while the fabrication process thereof is outlined in FIG. 6. The device of FIGS. 1-3 includes several cavities 102 (e.g., approximately 500 microns wide, 1 mm long and 30 micrometers deep), which may have metallic thin-film heater elements 106 deposited (e.g., by sputtering) on the top surface. The film is titanium-platinum, with thickness 10 nm (e.g., for titanium) and 250 nm (e.g., for platinum). The film is patterned by photolithography to create wide metallic strips with narrow constrictions (e.g., 40 micrometer wide) at the center of the cavities 102. Consequently, when electric current is sent through the film, most of the heat is generated at the center of the constriction. This heater geometry, therefore, essentially acts as an "electrical point heater," the majority of the heat being released in a 40 micrometer-round area at the constriction.

FIG. 4 is a typical phase diagram of crude oil (e.g., modified from Bentancourt et al., "Analyzing Hydrocarbons in the Borehole," Oilfield Review, p. 54, Autumn, 2003). In FIG. 4, the bubble point curve 402 represents the locus of bubble point pressures at various temperatures. In this diagram, bubbles are unstable 404 (e.g., they collapse) above the BP pressure line 402, and are stable 406 (e.g., expand) below the BP pressure line 402. The inset shows the phase-space excursion of a sample in the proximity of the BP pressure line 402 where transient bubbles are created by ultrasonic cavitation, and, respectively, by thermal nucleation.

Crude oils are mixtures of many components, from light gases, such as methane and carbon dioxide to extremely heavy compounds, such as asphaltenes and waxes. The BP curve 402 delimits the regions of the phase diagram where a separate gas phase is stable (e.g., low pressure) from those where it is not (e.g., high pressure). It ends at a critical point 406 of the fluid mixture, above which it becomes the dew point curve. The exemplary embodiments are concerned mostly with behavior at temperatures below the critical point 406 so the BP curve 402 is the only relevant one. As pressure is dropped through the BP curve 402 at constant temperature, bubbles develop. The full phase behavior of such mixtures is described in several texts, including Johanna Levelt Sengers, "How Fluids Unmix: Discoveries by the School of Van der Waals and Kamerlingh Onnes," Royal Netherlands Academy of Arts and Sciences, 2002 and of particular note is a concise review in the previously discussed text of Betancourt et al., and all of which texts are incorporated by reference herein.

During a cavitation experiment in proximity to the bubble point, pressure is dropped transiently (e.g., by means of a revolving propeller or of an ultrasonic actuator) to below the BP pressure (e.g., sometimes significantly so). Bubbles can therefore nucleate and then behave according to the original position of the sample in the phase diagram. For example, if the original experiment was initiated with the sample above the bubble point pressure, then the bubbles will shrink, otherwise they will be stable or even expand. A vertical arrow 408 in the inset to FIG. 4 shows the phase-space excursion seen by a sample during the cavitation experiment.

There is more than one way, however, to cross the bubble point curve 402. The bubble point curve 402 can also be crossed horizontally in the P-T phase-space diagram as shown with a horizontal arrow 410, again resulting in nucleation of bubbles. Such a horizontal phase space trajectory corresponds to heating the sample. Normally, in the petroleum industry, bulk heating of the sample is not desired because this changes the BP pressure of the sample. Extremely localized heating, however, only minimally affects the average temperature of the bulk sample—in micro-fluidic devices for example (e.g., where fluid travels through channels having dimensions of only tens to hundreds of micrometers), the large surface-to-volume ratio assures extremely fast thermal equilibration times of the fluid with the surroundings. If a heat pulse is applied locally to a very small volume of fluid, it can generate very large local temperature fluctuations (e.g., corresponding to a large displacement to the right in the phase-space diagram of FIG. 4), resulting in immediate bubble nucleation. As soon as the heat pulse ends, the sample re-equilibrates to bulk temperature in a matter of milliseconds. Depending on the relation of the sample pressure to the bubble point pressure, the generated bubbles will shrink or expand. The device of FIGS. 1-3 can be used to provide such localized heating and heat pulse. Thus, in one embodiment, the apparatus and process of this invention can be implemented with bulk fluid (e.g., a stream of oil produced in a well) by extracting a sample of the oil, nucleating and detecting at least one bubble in the apparatus of FIGS. 1-3, and/or determining the BP pressure of the sample in the process and apparatus of FIGS. 14 and 15 or any other suitable devices described herein.

Figure 5A:
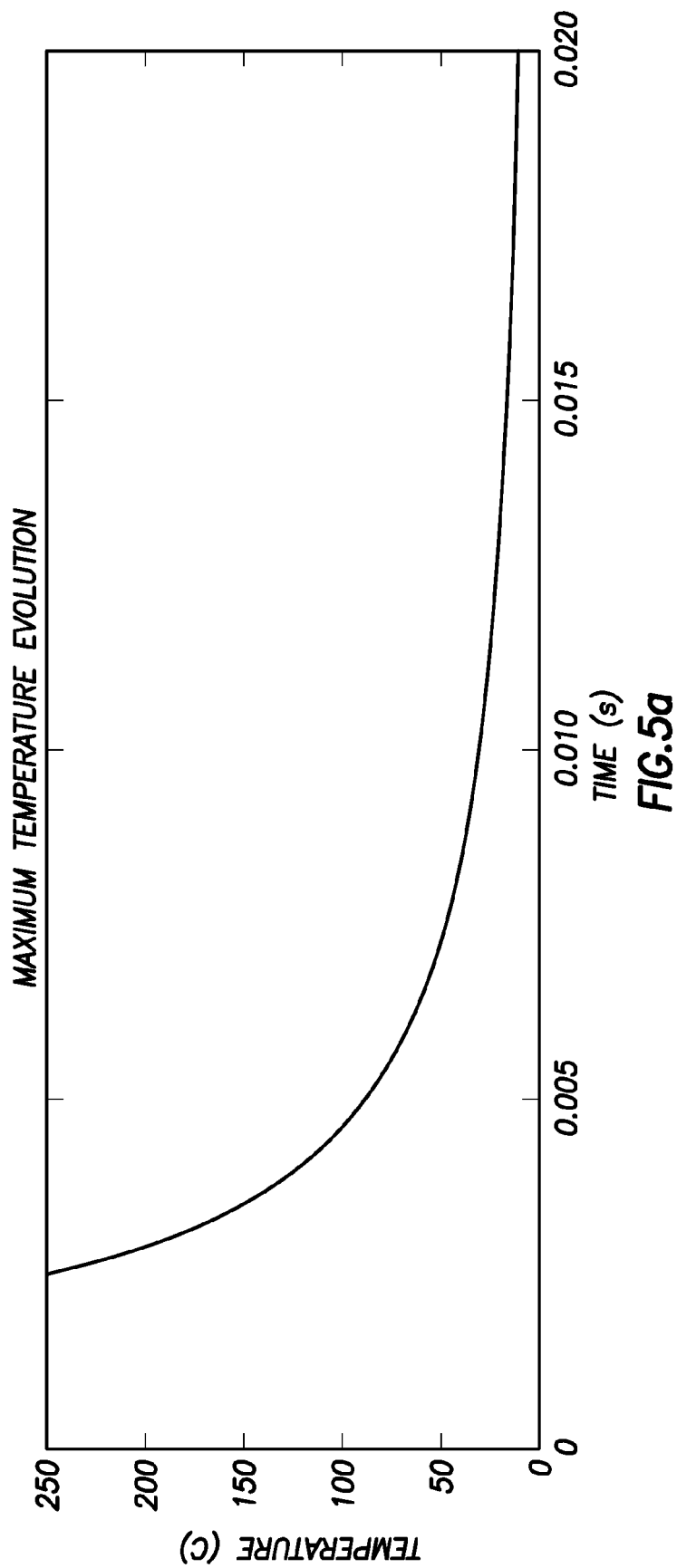

In an extension of the above exemplary embodiments, the exemplary device, such as that of FIGS. 1-3, can be combined with additional heating and active cooling elements placed on, or around the bubble point measurement device and suitable for heating and cooling the whole device, including the bulk fluid in the cavity. This, combined with the ability to manipulate the fluid pressure, advantageously, allows calculation of the bubble point at multiple temperatures—thus constructing a phase diagram (e.g., as shown in FIG. 4) for the fluid being analyzed. In one implementation, the measurement device is a micro-fluidic device, and the small volume of the device, as well as the small volume of the sample being analyzed in the cavity of the device, e.g., a micro-fabricated chamber 102, would allow for rapid heating and cooling of the device and fluid. Accordingly, by slowly varying the bulk temperature of the measurement device, and consequently of the sample, and measuring the BP pressure at different temperatures by the methods described herein, the bubble point curve 402, separating the single- and multi-phase regions in the phase diagram shown in FIG. 4, can be calculated. FIGS. 5a and 5b graph the simulated dependence of temperature on time within the central part of the cavity 102. The device modeled in these simulations is the same as that shown in FIGS. 1-3. In FIGS. 5*a* and 5*b*, an amount of 2 millijoules of thermal energy is injected in the heater 106 quasi—instantaneously. The graph of FIG. 5*b* shows the temperature profiles in the cavity 102, subsequent to the heating pulse, with curves 502-512 for times ranging from 2 milliseconds (ms) to 100 ms, respectively. The graph of FIG. 5*a* shows the time dependence of the maximum temperature in the cavity 102 (e.g., which occurs at the center of the heater 106). As can be seen, the temperature decays rapidly (e.g., with a temperature equilibration time of a few tens of milliseconds) to ambient temperature, which is set to 0 degrees for this simulation.

FIG. 6 illustrates fabrication of the exemplary bubble-point sensor of FIGS. 1-3. The various fabrication steps include: S0—cleaning of a high-purity, high resistivity, Si wafer; S1—aluminum deposition and lithographic patterning; S2—dry reactive ion etching (e.g., DRIE) of Si front side; S3—DRIE back side (e.g., through-holes); S4—Al removal; G0—cleaning of glass wafer (e.g., Pyrex); G1—photoresist protection and lithographic patterning; G2—glass wet etching (e.g., hydrofluoric acid solution); G3—metal evaporation (e.g., Ti—Pt); G4—photoresist removal/metal liftoff; Final assembly—the wafers are anodically bonded, diced, fluidic ports and electrical connections are attached using epoxy rings and wire-bonding, respectively.

The resistance of the heater 106 is approximately 3 Ohms. A DC electric current pulse of approximately 0.33 Amperes and with a duration of approximately 5 milliseconds is sent through the heater 106, resulting in a dissipation of approximately 2 millijoules of thermal energy (e.g., the number used in the above simulations). The current can be set at a higher or lower value and the length of the pulse can also be adjusted to inject other amounts of heat over other durations (e.g., which can affect the process of bubble nucleation). As seen in FIG. 5, an abrupt increase in temperature occurs at the heater 106 (e.g., by approximately 200 degrees C.), resulting in nucleation of a bubble centered at the heater 106.

EXAMPLE 1

With Pure Ethanol

Figure 7:
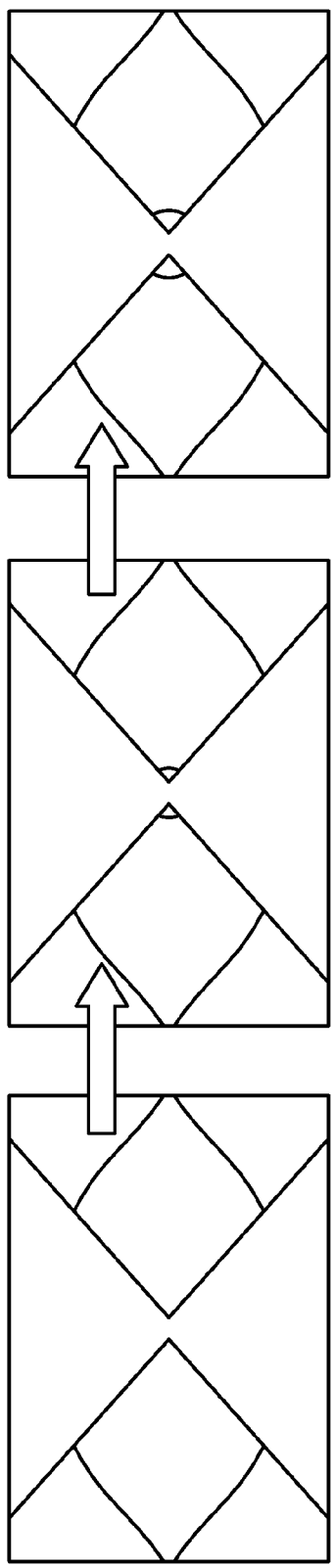
FIG. 7 illustrate exemplary micrographs of an exemplary thermal bubble nucleation process using ethanol as a sample fluid.

Exemplary experiments are a simple illustration of the overall principle of the exemplary devices, and were performed at atmospheric and sub-atmospheric pressures using ethanol as the working fluid. Micrographs of the thermal bubble nucleation process using ethanol as the sample fluid are shown in FIG. 7. In FIG. 7, bubble nucleation by heating with the exemplary micro-fabricated heater is shown with a heating power of approximately 500 mW continuously applied to the heater 106, and with the images spaced 10 milliseconds apart. The ethanol was thoroughly degassed in a vacuum dessicator prior to performing any experiments. This allowed a large portion of the dissolved gas (e.g., mostly air) to escape; some dissolved gas remained in the ethanol. The ethanol was injected in the exemplary device, described above in conjunction with FIGS. 1-3, and 5-7, which was in turn connected to a vacuum pump allowing the ambient pressure to be controlled. Using a thermal pulse from the integrated electrical heater 106, a gas bubble was nucleated in the cavity 102. When pressure is set below bubble point (which for a pure fluid like ethanol corresponds to the vapor pressure at ambient temperature), nucleated bubbles grow; if the pressure is set above the bubble point, the bubbles shrink.

The nucleated bubbles were allowed to grow slowly, while maintaining a reduced pressure, and the heater 106 and cavity 102 were allowed to cool to ambient temperature. This also allowed the bubble to move away from the center of the heater 106 so that it can be tracked visually, for example, using any suitable automated algorithms. Once the cavity thermally equilibrated, the external pressure was changed and the behavior recorded. To quantitatively measure the effects of this pressure change on bubble behavior, a high speed video capture system was used to record the nucleation and subsequent growth or shrinking of the bubbles.

Figure 8:
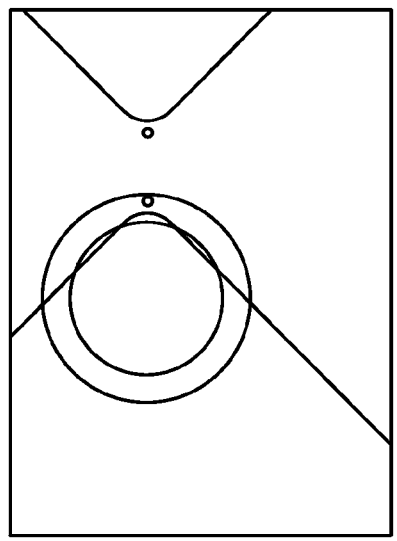
FIG. 8 illustrates employing particle tracking algorithms to calculate bubble radius in each observed frame.

Using particle tracking algorithms, the bubble radius was calculated for each frame, as shown in FIG. 8. In FIG. 8, a bubble is being tracked, and due to the small depth of the cavity (30 microns) compared to the bubble diameter (in this case approximately 120 microns), the bubble is flat like a pancake. Inside the inner circle, the bubble is flat against the chamber top and bottom.

Figure 9A:
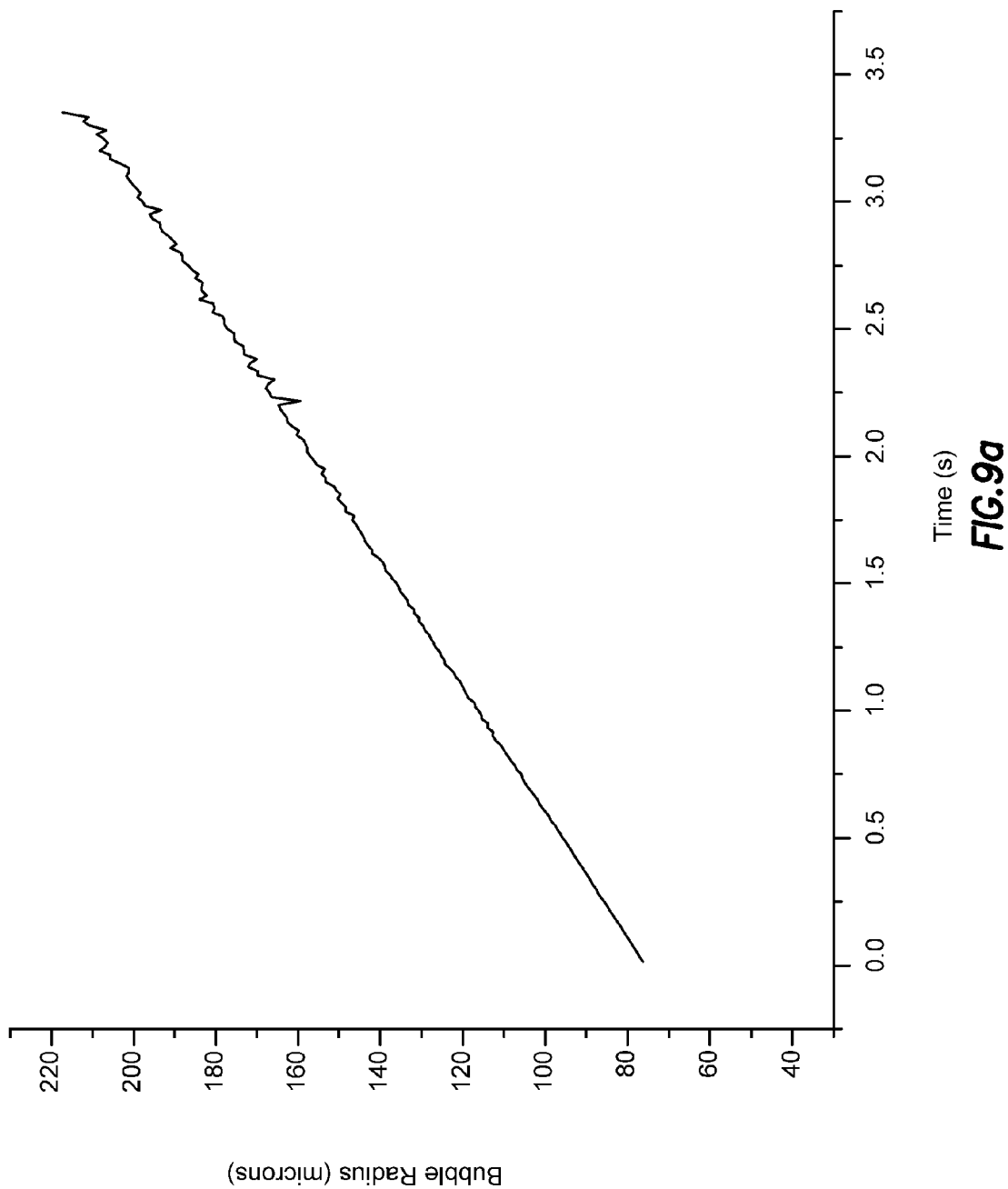
FIGS. 9a-9b illustrate linear behavior for growing and shrinking bubbles.
Figure 9B:
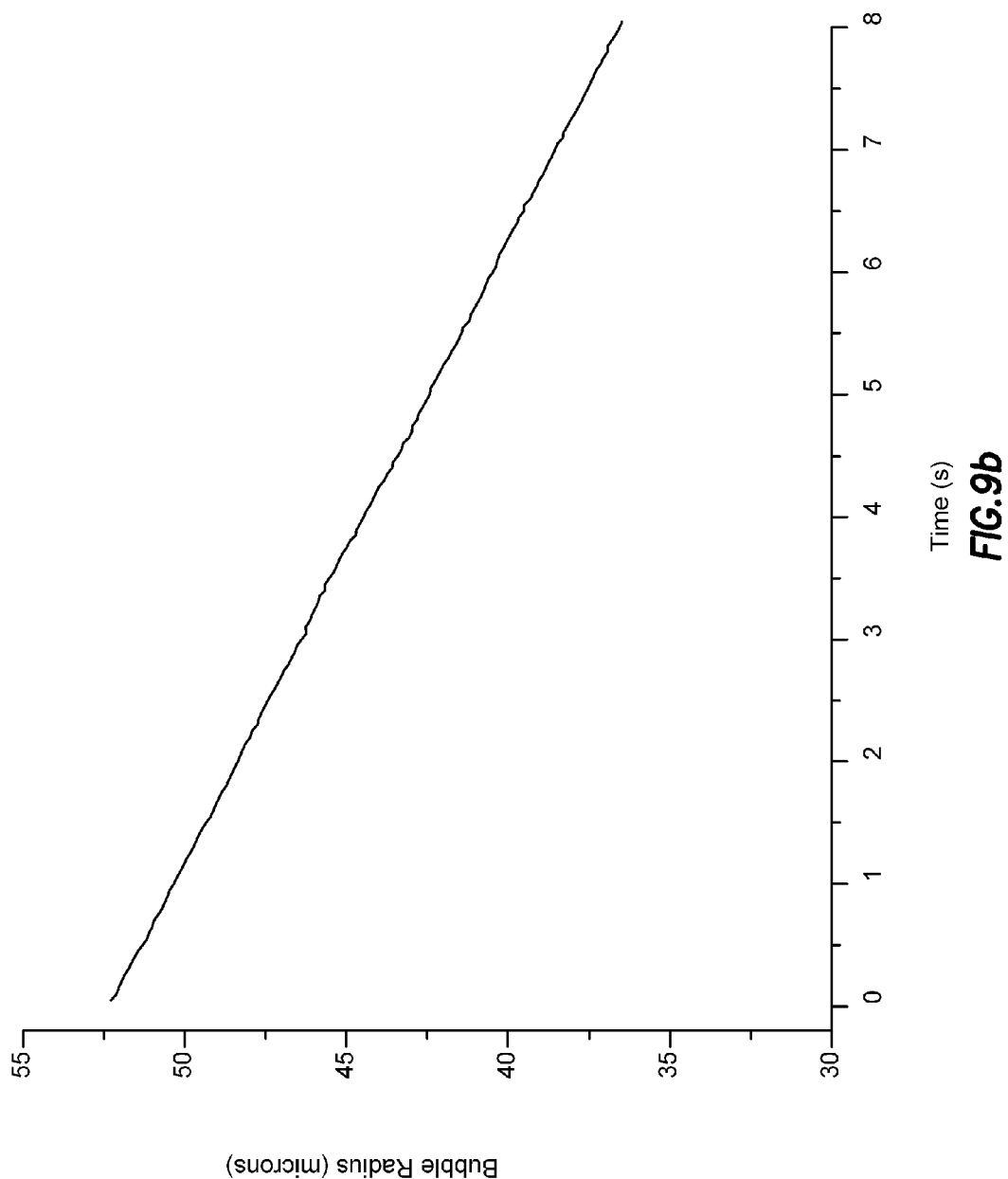

Similar linear behavior for growing and shrinking bubbles was observed in both cases, as shown in FIGS. 9*a* and 9*b*. In FIGS. 9*a* and 9*b*, linear bubble growth is shown, using ethanol as a working fluid. For ambient pressures below the solution bubble point, there is growth (FIG. 9*a*). Above the bubble point, the bubble shrinks in size (FIG. 9*b*). Both behaviors are linear with time, suggesting that in this case the behavior is interface limited.

In FIGS. 9*a* and 9*b*, the channel height is approximately 30 microns, so for both of these bubbles the dynamics are essentially two-dimensional. If the internal bubble pressure were constant and equal to the ethanol vapor pressure, the pressure drop from the bubble to the surroundings would be constant and the flow rate would then also be constant (e.g., assuming that the flow of fluid is laminar). For a two-dimensional bubble with volume approximated by $\pi r^2 h$ (where r is the radius, and h is the height of the bubble), this would give growth that varies as a function of $t^{1/2}$ (where t is the time). If, instead, the growth were limited by diffusion at the bubble interface, which may have an area given by approximately $2\pi rh$ in the two-dimensional geometry, then the flow rate would vary as a function of radius and the radial growth rate would be approximately linear in time. The equilibration between ethanol and its vapor is well known and is significantly faster than the rates observed here. This suggests that the bubble dynamics are indeed controlled by interface diffusion of dissolved gas (such as, e.g., oxygen, carbon dioxide, nitrogen, and the like), which has significantly slower dynamics at the interface.

Figure 10A:
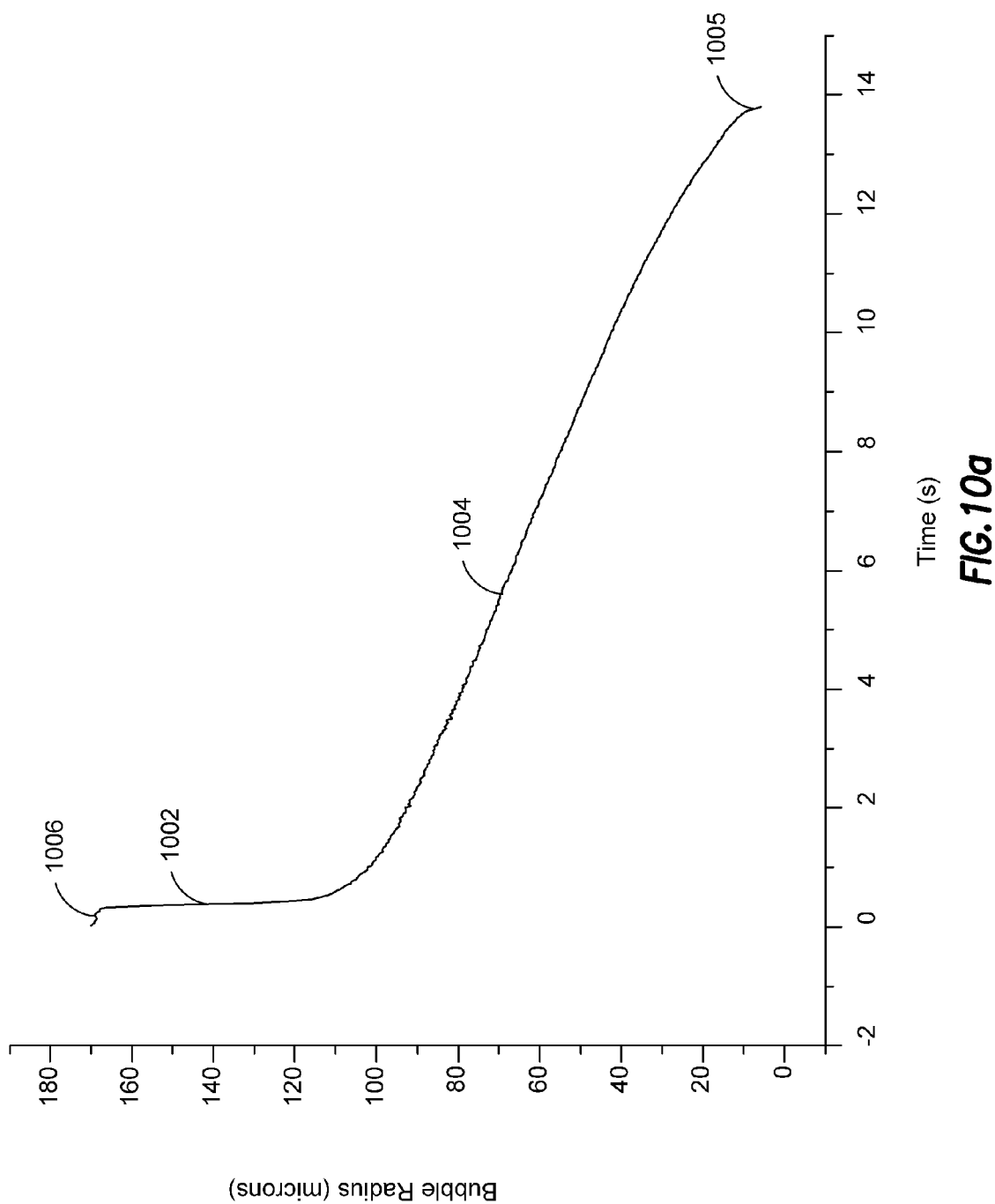
FIGS. 10a-10b illustrate bubble dynamics using ethanol as working fluid.

As further demonstration of these principles and observations, the pressure was rapidly increased by removing the vacuum pump. The behavior of the bubble is recorded on the graph of FIG. 10*a*, wherein the increase in pressure is shown at 1006. The bubble shows a fast compression at 1002, limited by the viscous drag on fluid pulled in to fill in the bubble, and once the pressure has equilibrated, the gas slowly dissolves into the liquid at 1004 until the bubble finally collapses and disappears at 1005.

Figure 10B:
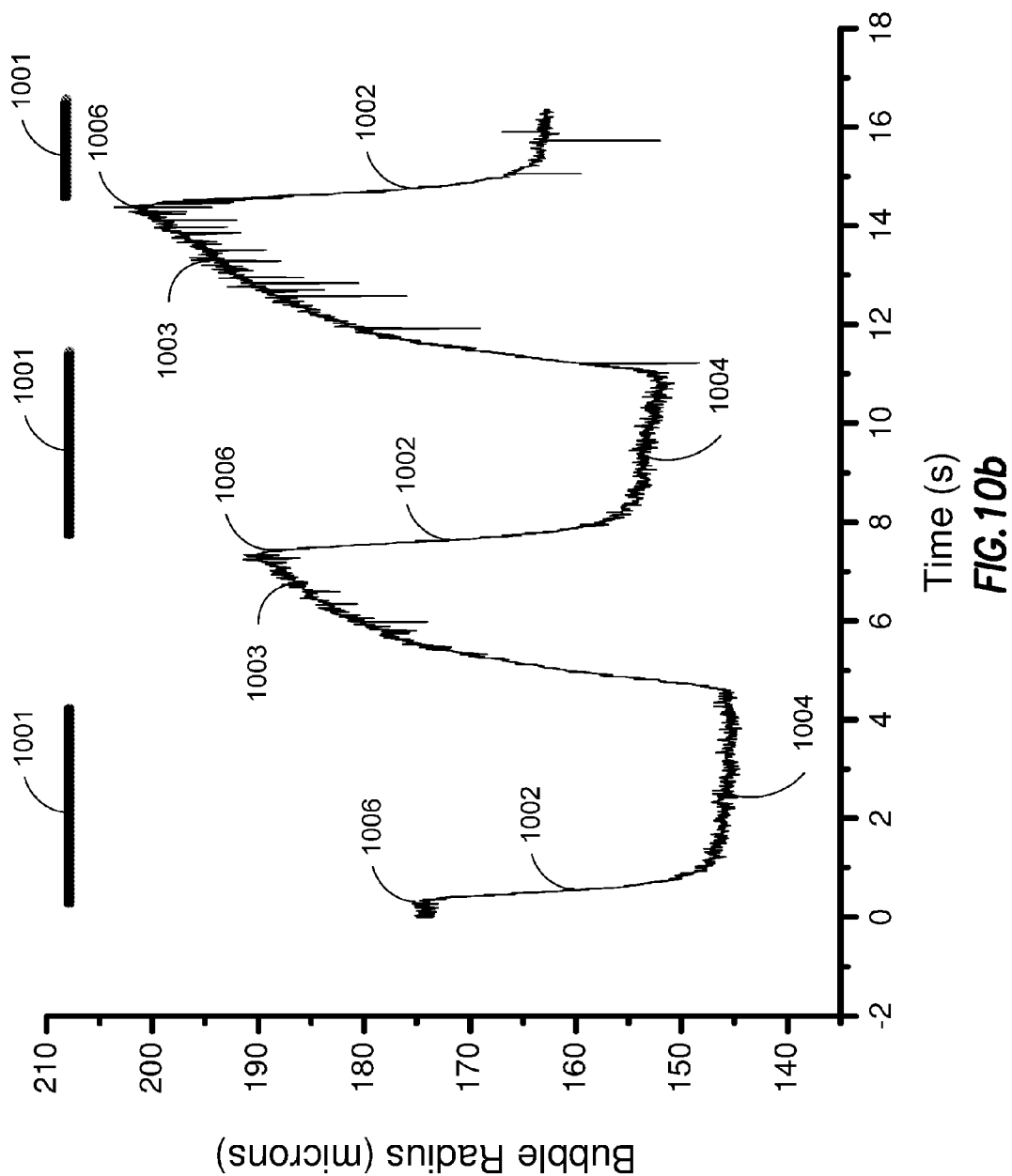

This process can be repeated cyclically to show the same general behavior, as shown in FIG. 10*b*. In FIG. 10*b*, bubble dynamics is shown, using ethanol as a working fluid. When subjected to a sudden increase in pressure at 1006, there is a fast decay at 1002, corresponding to compression, followed by gas slowly dissolving back into the ethanol at 1004. When the pressure is decreased again by connecting the vacuum pump to the outlet of the device, the bubble starts growing again gradually at 1003. Accordingly, when subjected to pressure pulses at 1001, the behavior is similar, cyclical and very reproducible, as shown in FIG. 10*b*.

EXAMPLE 2

With a Hexadecane-$CO_2$ Mixture

To simulate better the environment likely to be encountered in a down-hole situation, in an exemplary embodiment, a sample of hydrocarbon oil that was saturated with pressurized gas was created. $C_{16}$ (hexadecane) was employed as the oil (e.g., also referred to herein as "$C_{16}$ oil") and it was pressurized with $CO_2$ for many hours, while thoroughly mixing the sample. This created a sample of oil saturated with dissolved gas at a given gas pressure, which also corresponds to the BP pressure of the sample.

Figure 11:
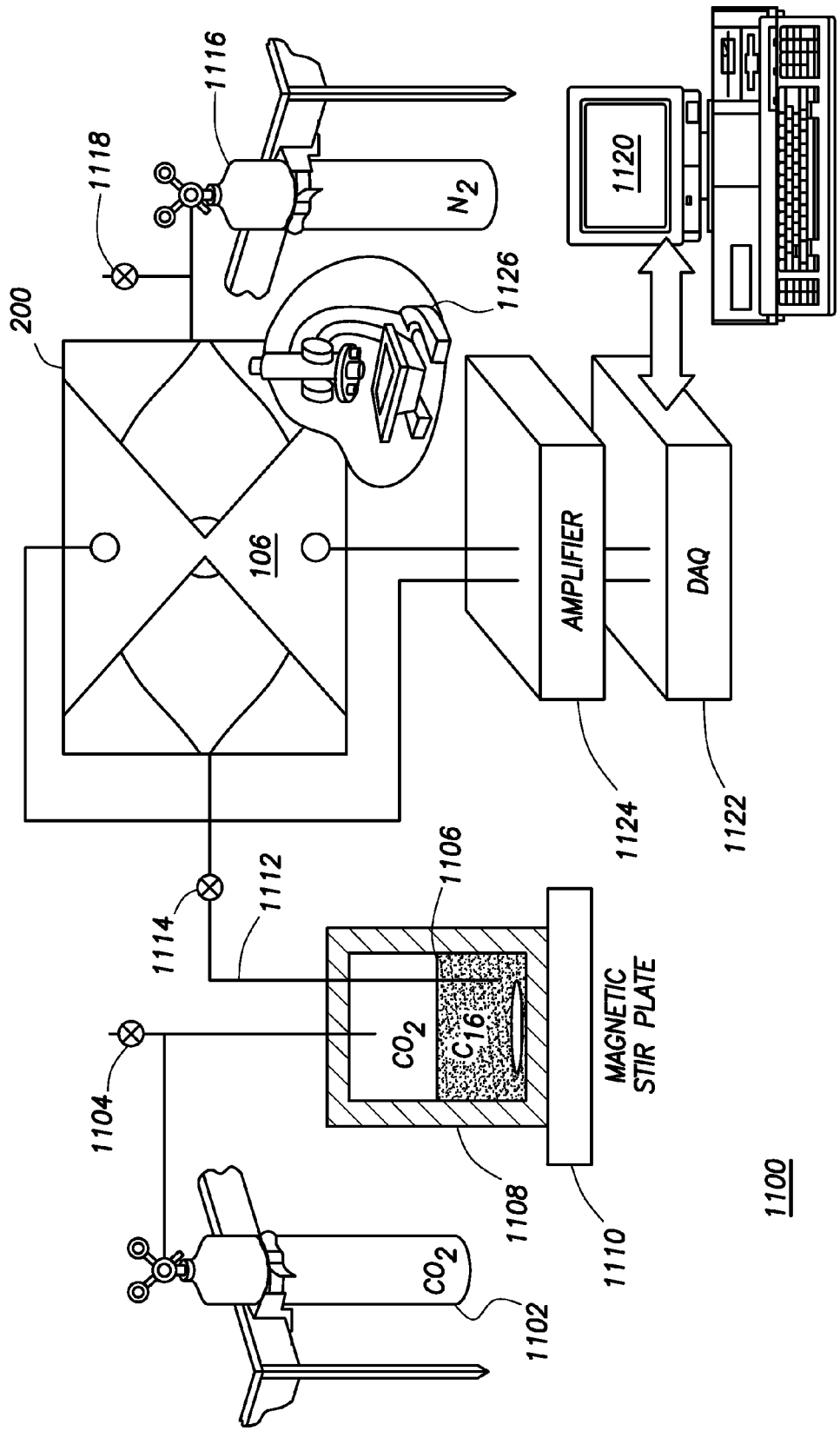
FIG. 11 illustrates an exemplary bubble point measurement system.

In one experiment, the $C_{16}$ oil was saturated with $CO_2$ at a pressure of 100 psi at room temperature (a time of 24 hours of continuous stirring was employed to achieve equilibrium). The sample was transferred from the pressure vessel into the micro-fabricated bubble point detector, while maintaining a backpressure of nitrogen gas. The bubble point detector was then isolated from the pressure chamber by closing a needle valve, and the nitrogen pressure was adjusted to maintain a desired pressure in the sensor. FIG. 11 depicts the system used for this experiment.

In FIG. 11, the exemplary bubble point measurement system 1100 includes a $CO_2$ source 1102 with a valve 1104, a $C_{16}$—$CO_2$ mixture 1106 prepared in a pressure vessel 1108, under constant agitation by a magnetic stir plate 1110 for approximately 24 hours. A known equilibrium $CO_2$ concentration in the solution 1106 was achieved by regulating the gas pressure via the valve 1104. A small amount of the sample was transferred via a capillary, or capillary tube 1112 and a sample valve 1114 to the micro-fluidic bubble point detector 200 (e.g., substantially the same as that of FIGS. 1-3), under pressure. The sample valve 1114 then was closed, and the pressure of the sample could then be adjusted by changing $N_2$ source 1116 back pressure via valve 1118. Using a computer 1120 connected to a data acquisition board 1122, voltage pulses via an amplifier 1124 were applied to the micro-fabricated heater 106. The behavior of the nucleated bubbles could then be recorded, for example, via fast video microscopy 1126 or detected or monitored by using a heater element 106 as a thermal conductivity bubble detector.

In an exemplary embodiment, a high initial nitrogen pressure (130 psi) was introduced, which was higher than the BP pressure of the sample (100 psi). The $N_2$ pressure was then slowly decreased, and short voltage pulses on heater 106 were generated (each pulse was 5 milliseconds long, generating a total of approximately 2 millijoules of thermal energy). As can be seen in the simulation of FIG. 5b, such short pulses generated a very abrupt temperature spike centered at the heater 106, resulting in bubble nucleation. The fluid immediately re-equilibrated at ambient temperature (e.g., within a few tens of milliseconds, as shown in the simulation in FIG. 5a). Bubble behavior was video-recorded, for example, using an inverted microscope coupled to a fast frame grabber. In further exemplary embodiments, a bubble detector based on thermal conductivity, optical density, index of refraction, and/or similar principles, can be employed, as discussed herein.

Figure 12:
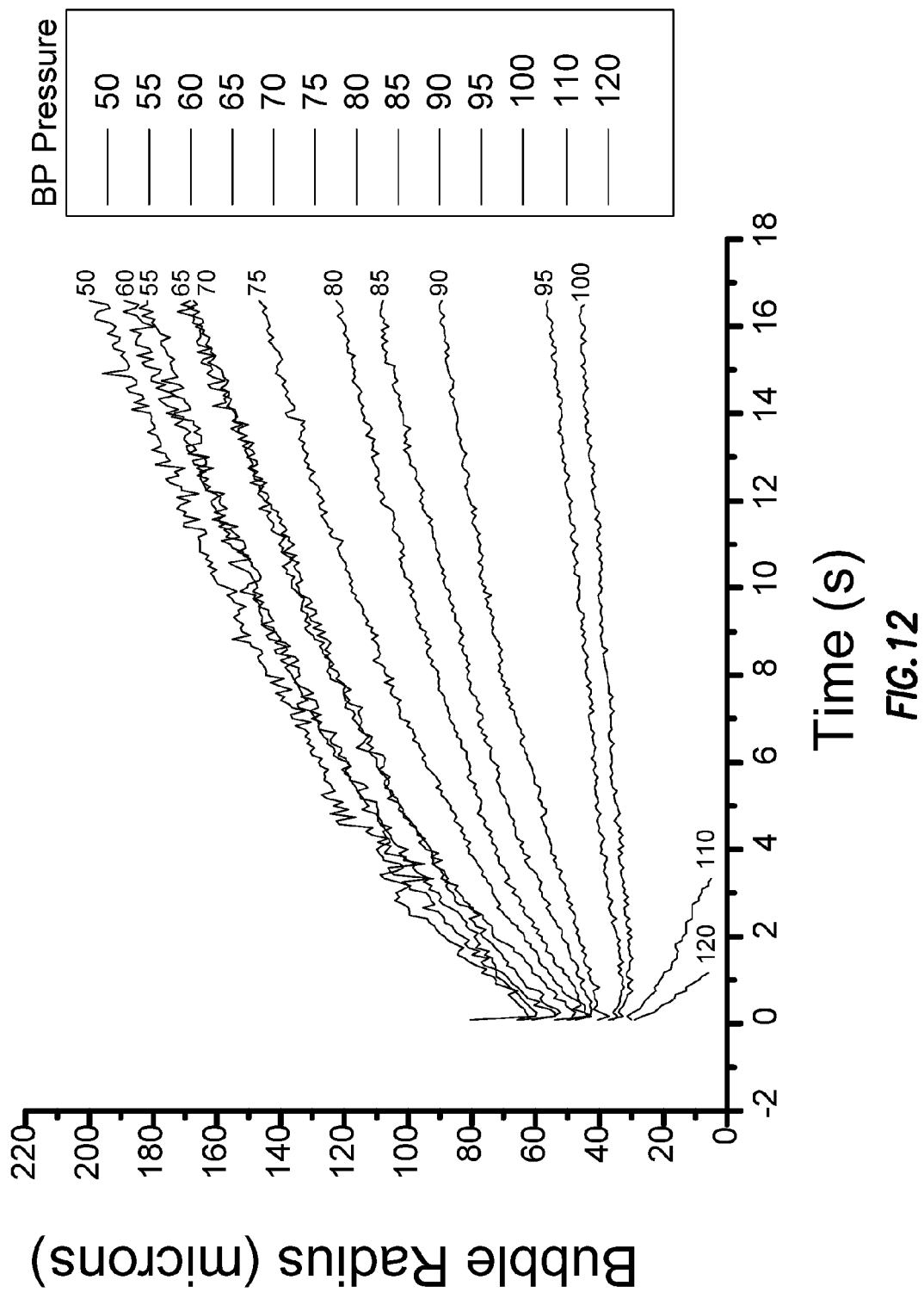
FIG. 12 summarizes nucleated bubble behavior for various sample pressures.

The nucleated bubble behavior for various sample pressures is summarized in FIG. 12. In FIG. 12, bubble behavior after nucleation depends on the value of the ambient pressure relative to the BP pressure of the sample (in this case, 100 psi). FIG. 12 shows bubble behavior for various bubble point pressures, ranging from 120 psi (lowest curve) to 50 psi (highest curve). As can be seen from FIG. 12, for pressures below the bubble point pressure, the nucleated bubbles grow (radius increases over time), and growth velocity increases with decreasing pressure below bubble point. For pressures above the BP pressure, nucleated bubbles shrink and eventually disappear (radius reduces to 0). It is interesting to note that the radius of the bubble at t=0, the moment of nucleation (40-60 microns) is comparable in size with the active region of the heater (40 microns).

In FIG. 12, the bubbles are nucleated at t=0 (with a 5 ms heating pulse), and then undergo a shrinkage of 10-20% in the first 25 ms after the heat pulse. After the initial rapid shrinking stage, the bubbles start growing or continue shrinking depending on the value of the ambient pressure relative to bubble point pressure. Although the bubble growth or shrinkage rates do not appear to be perfectly linear with time, FIG. 12 shows that bubbles grow/shrink faster the farther pressure is from the bubble point pressure. While growth and shrinkage rates are not universal (e.g., they depend on the geometry of the device, the composition of the sample, and on other interfacial properties, such as concentration of surfactants), the trends seen in FIG. 12 are quite exemplary and do qualitatively capture the bubble behavior. Similar behavior was observed for samples equilibrated at other pressures, as the pressure is externally varied through the bubble point pressure.

In the above exemplary experiments, bubbles can be detected optically, for example, using a microscope coupled to a fast camera, and the like. This is a very useful setup for lab experiments, as it enables detailed studies of bubble nucleation and evolution. From a sensor perspective, however, the setup can be relatively expensive and employ significant amount of tool volume, optical components, disk storage, and computational power, and thus can be impractical for making a practical downhole BP pressure sensor. Accordingly, a simple and integrated way to detect the presence of bubbles downhole, and perhaps measure certain properties thereof (e.g., such as the radius, or the chemical composition) is needed. In addition, there are several physical and chemical intrinsic properties that can differentiate gas from liquid, for example, including thermal conductivity, optical density, index of refraction, density, viscosity, chemical composition, dielectric constant, electrical conductivity, compressibility, and the like. In order to detect a bubble, one or several of these properties can be monitored with specific sensors.

Figure 13:
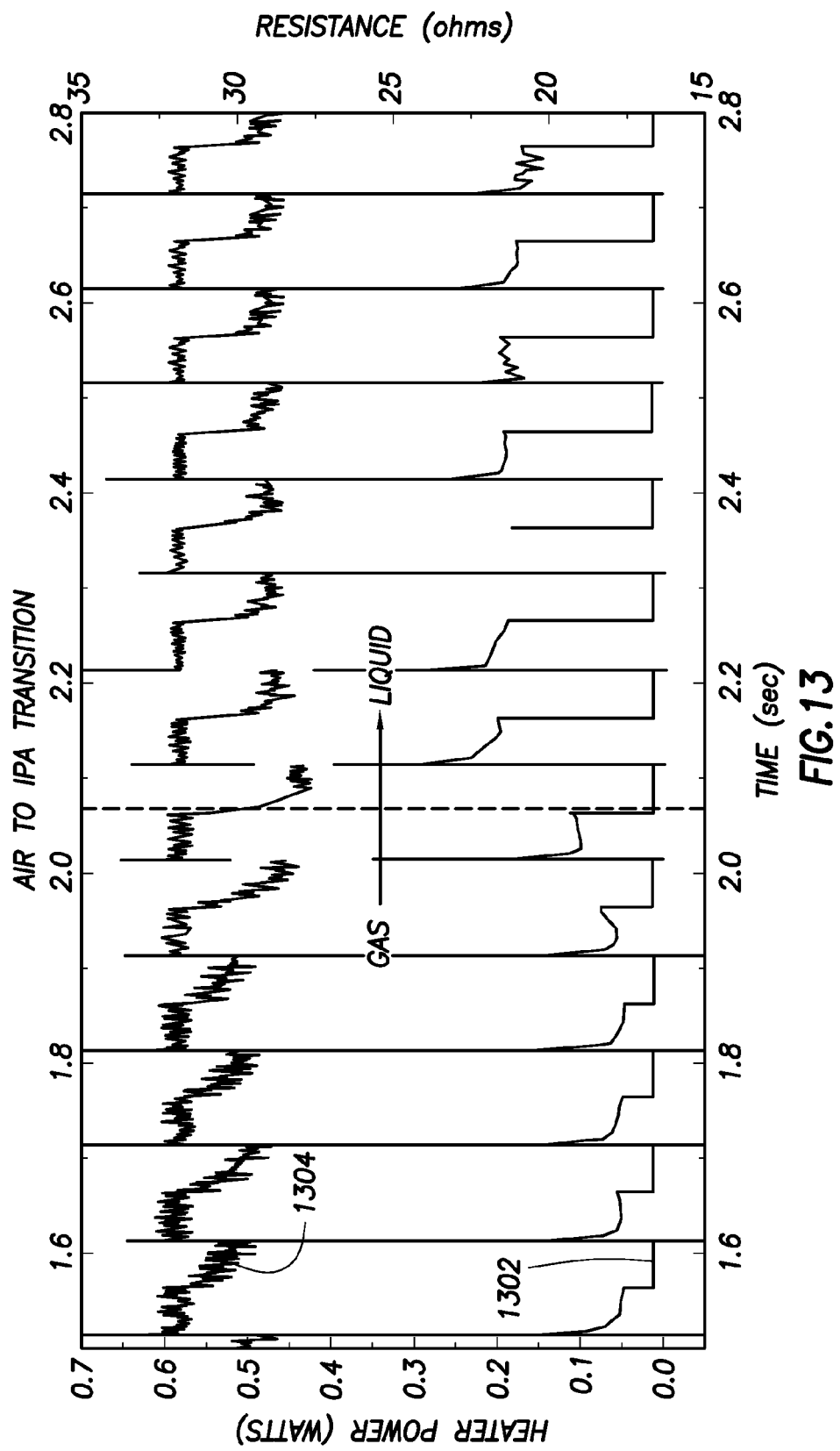
FIG. 13 illustrates operation of a bubble point detector.

A measurement that can be implemented to detect a bubble is a thermal conductivity measurement (which also can be referred to herein as a "thermal technique"). For example, such embodiment employs a closed feedback loop, wherein a heater or other thermal device can be maintained at a certain constant temperature above the ambient temperature of the surrounding fluid. The amount of power required for this operation can be constantly monitored. The heater power depends on the ability of the surrounding fluid to transport heat away from the heater (e.g., on the thermal properties of the medium). The heater power provides therefore a measure of thermal conductivity, and hence a way to differentiate gas (e.g., such as inside a bubble) from liquid. More specifically, this monitored power consumption can be used to distinguish a low thermal conductivity from a moderate thermal conductivity fluid and further from a high thermal conductivity fluid. Examples of low thermal conductivity fluid are gasses. Examples of fluids with moderate thermal conductivity are fluids like hydrocarbon oils and examples of fluids with high thermal conductivity are fluids such as water. A heater operated in this mode can therefore be used as a phase-detection mechanism. FIG. 13 demonstrates the operation of such a detector, as described in United States Patent Application Publication No. 20070061093 to Angelescu et al., entitled "Time-of-Flight Stochastic Correlation Measurements,"

("U.S. Patent Publication '093"), and incorporated by reference herein. It is apparent that heater power depends on the phase of the fluid flowing by the heater, namely high power, fast decay for liquid and low power, slow decay for gas. The constant-temperature heater can therefore also be used as an oil-gas detector in multi-phase flow. This method has the advantage that the same heater element used to nucleate a bubble can be used to detect the bubble as well, i.e., operating as a transducer. However, any other suitable method can be employed to detect the bubbles.

In FIG. 13, the amount of power required to run a heater in constant temperature mode depends on the thermal conductivity of the medium surrounding the heater. This is a reliable way to differentiate between gas (e.g., low thermal conductivity) and liquid (e.g., high thermal conductivity). The heater power trace 1302 versus resistance 1304 in the graph of FIG. 13 shows clearly the transition from gas to liquid. As can be seen from FIG. 13, significantly more power is required to maintain a certain temperature of the heater when surrounded by liquid, as compared to gas.

Pressure Reduction Mechanism

In addition to bubble creation and detection, an exemplary BP pressure measurement system also can include means for changing sample pressure through the bubble point pressure. In the oilfield, an exemplary embodiment includes starting with a formation fluid mixture pressurized above its bubble point pressure, and depressurizing it slowly to measure its bubble point pressure. The ability to slowly depressurize the fluid is therefore employed for BP pressure measurement. A traditional lab technique used for this purpose includes using a piston to vary the volume (and hence the pressure) of a sample. This technique can still be used with a thermal BP sensor, as will be seen from additional examples to follow. The following exemplary embodiments, however, describe an alternate technique to achieve a similar outcome, by using viscous drag as a means to generate a pressure drop.

In an exemplary embodiment, a long series of chambers (e.g., similar to the one shown in FIG. 1) are connected in series by capillaries (e.g., similar to FIGS. 1-2), wherein such capillaries are preferably micro-fabricated. Each chamber incorporates a heater 106 and a bubble detector. In a further exemplary embodiment, the same heater 106 element(s) can be used as a transducer or transducers, to both nucleate the bubble and detect it. The detection is described in U.S. Patent Publication '093. A high-pressure fluid is connected to one end of the long line of chambers, while the other end is connected to an empty recipient (e.g., to be used as a "low pressure reservoir"). The fluid flowing through the chain of chambers creates a pressure gradient due to viscous drag, with each chamber having a pressure slightly lower than the previous and slightly higher than the next chamber. The first chamber can then be at the formation pressure, the last one at the pressure of the "low pressure reservoir" and chambers in between having intermediate pressure values. Due to the miniaturized dimensions of all the fluidic paths, flow through such a device is essentially laminar, so that the pressure at any point in the chain of connected chambers can be determined, for example, by methods of interpolation, extrapolation, and the like. Making a reliable pressure interpolation or extrapolation using this technique employs the fluid in single-phase condition in the region where the interpolation or extrapolation is applied, and the pressure is measured at two or more different points situated upstream of the chamber where the sample reaches BP pressure. This ensures that the sample is contained between the pressure measurement points and all the way to the chamber where the BP pressure is crossed is in a single-phase condition.

Figure 14:
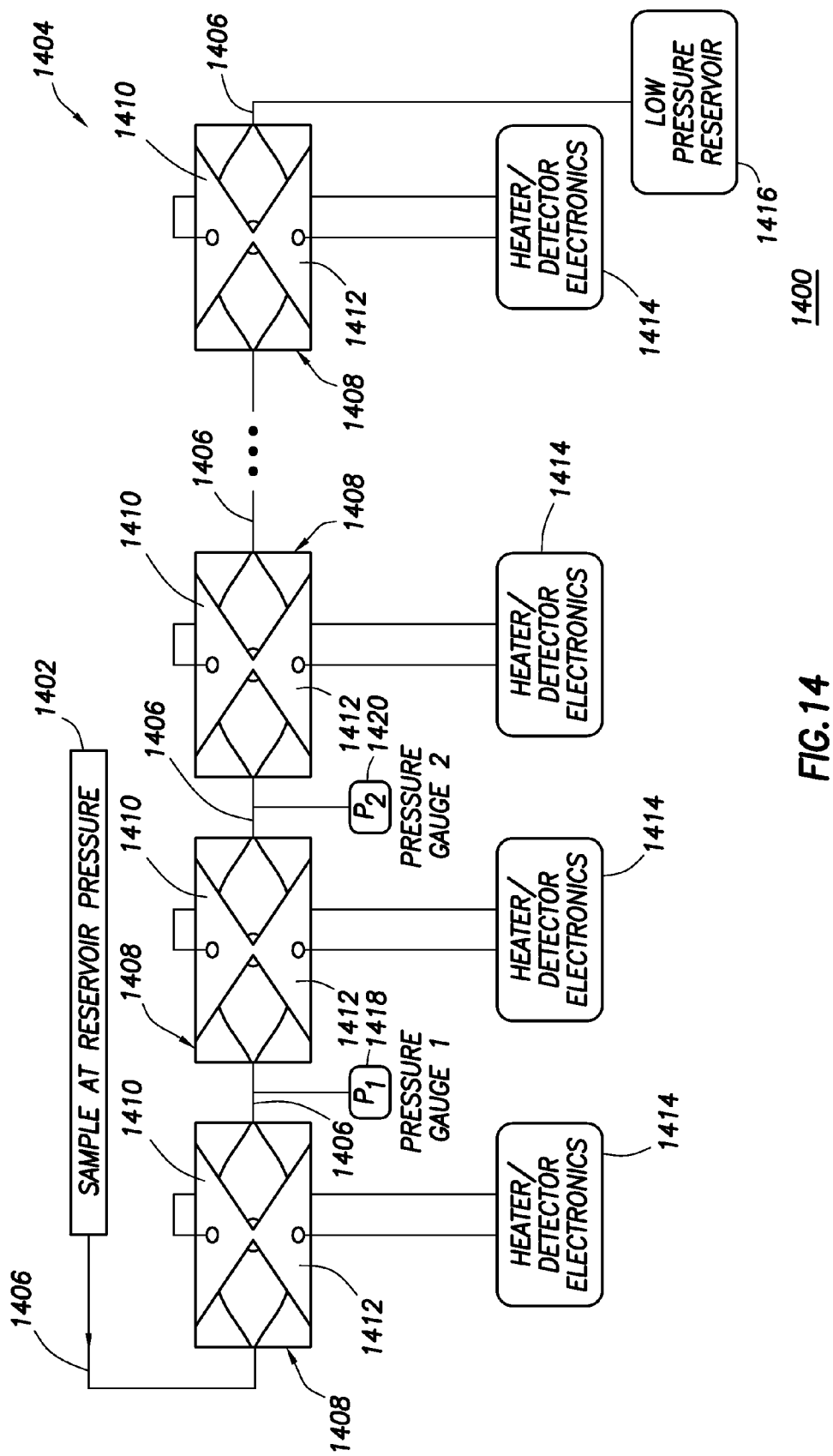
FIG. 14 illustrates a complete exemplary bubble point measurement system.

FIG. 14 schematically illustrates such a complete exemplary BP pressure measurement system 1400, advantageously, having no moving parts. In FIG. 14, a sample 1402, initially at reservoir pressure, is introduced in a long chain of micro-fluidic chambers 1408 connected in series with capillaries 1406. Each chamber 1408 may have a heater 1410/detector 1412 pair, controlled by dedicated electronics 1414. In an exemplary embodiment, the heater element 1410 and detector element 1412 can be the same device, wherein the device operation is switched alternatively between operation as a heater to nucleate a bubble and operation as a detector to monitor the behavior of the previously-nucleated bubble. The other end of the chamber chain is connected to a low pressure reservoir 1416, for example, which essentially can be an empty container of large volume compared to the volume of the micro-fluidic device, or it can be a device maintained by any suitable external means at a pressure lower than the BP pressure of the sample. Pressure gauges or sensors 1418 and 1420 (and, e.g., other pressure gauges or sensors disposed along the capillary) monitor the pressure drop along the chain of micro-fluidic chambers, which advantageously provides a way to interpolate the pressure in any chamber 1408 above the bubble point pressure.

If the low pressure reservoir 1416 is at a pressure below the bubble point pressure, and the sample reservoir pressure is above the bubble point pressure, then bubble point pressure will be crossed in one of the chambers 1408 in the chain. Based on the exemplary bubble nucleation-detection principle previously described, the chamber 1408 beyond which pressure is smaller than BP pressure can be identified. The pressure corresponding to that chamber 1408 can then be obtained by linear interpolation of the pressure measured at the two or more pressure gauges situated upstream of the chamber 1408, as described above.

In an exemplary embodiment, the two pressure measurements can be performed in the single-phase portion of the flow (e.g., at chambers with pressures superior to the bubble point pressure). Advantageously, this provides single-phase flow without bubbles between the two pressure measurement points, which results in a more accurate interpolation to determine bubble point pressure.

In addition, the size of the reservoir 1416 is configured so as to be large enough that its pressure will not rise significantly due to accumulation of gas bubbling from the outlet of the detector device or devices. The micro-fluidic size of the exemplary system 1400 is configured such that the capillary channels 1406 impose a limit on the flow rate, assuring that even a modestly sized reservoir (e.g., 1 liter, initially evacuated) can provide a pressure low enough for many hours of performing measurements. Thus, the chambers 1408 and the channels 1406 may have substantially the same dimensions and operate in substantially the same manner as discussed above for the apparatus of FIGS. 1-3.

Advantageously, the exemplary measurement scheme of FIG. 14 provides a BP pressure measurement technique without requiring any active mechanical parts, such as pistons, and the like. The simplicity of the technique and the miniaturized scale of the sensor make this invention attractive for downhole tool implementation of a BP pressure measurement system.

Complete BP Measurement System

Figure 15:
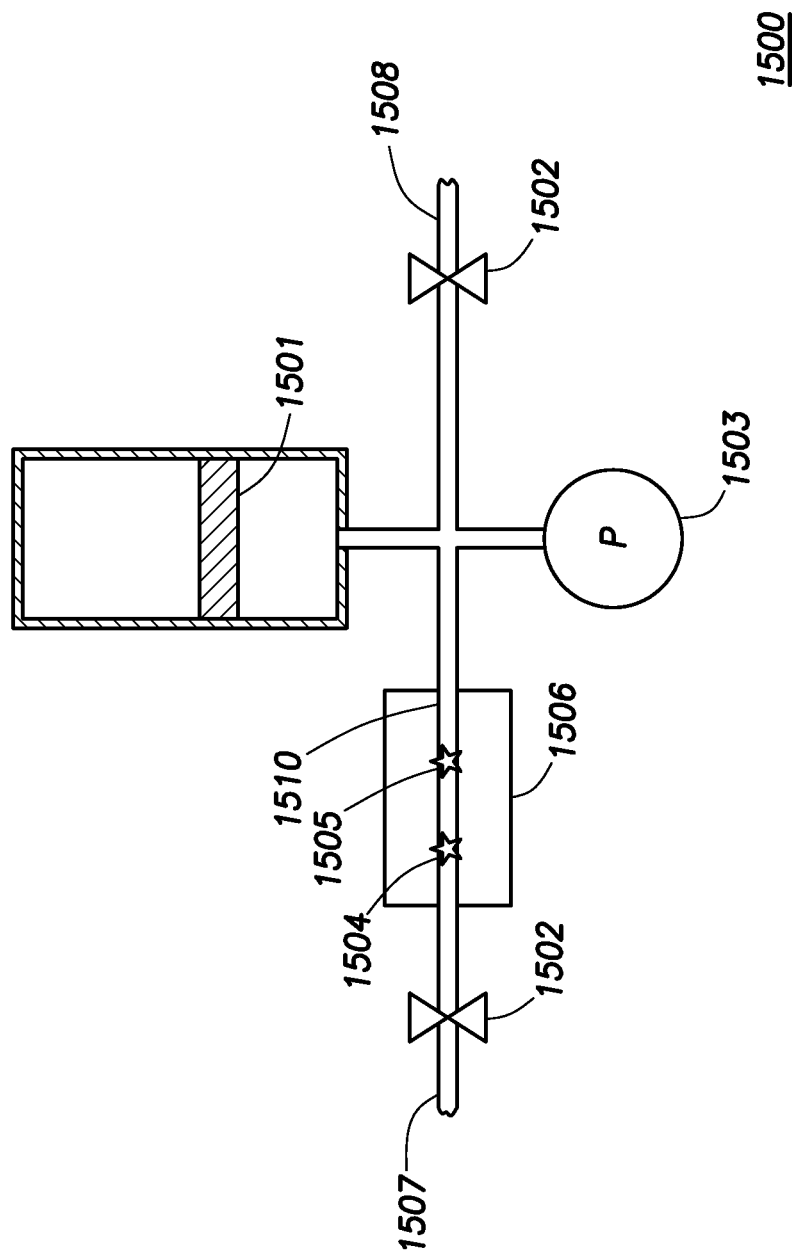
FIG. 15 illustrates an alternative embodiment of the exemplary bubble point measurement system of FIG. 14.

FIG. 15 shows a complete system 1500 for pressure reduction and BP pressure thermal detection, according to a further exemplary embodiment. In FIG. 15, the system 1500 includes a sample inlet 1507, a sample outlet 1508, two valves 1502 for separating a sample from the inlet 1507 and the outlet 1508, respectively, an externally actuated and controlled piston

1501 (or e.g., an externally actuated and controlled diaphragm or system of bellows, etc.) used to vary the pressure of the sample, a pressure gauge 1503 used to monitor and record the pressure of the sample, and a micro-fluidic BP detector 1506, including a heater 1504 and a thermal conductivity detector 1505 situated within a micro-channel 1510. The detector 1505 is situated downstream from the heater 1504, so that bubbles nucleated by the heater 1504 are forced by the flow in the micro-channel 1510 to move in front of the detector 1505.

An experimental procedure was performed, and included creating a sample of hexadecane oil saturated with carbon dioxide gas at a known pressure (e.g., equal to the BP pressure of the sample, in this case 950 psi), using the procedures previously described. The experiment continued by flowing a small amount of the sample through the exemplary system 1500 of FIG. 15, isolating a small amount of the sample between the valves 1502, and moving the piston 1501 at a constant, controlled, rate, while monitoring the pressure. The heater 1504 and detector 1505 were micro-fabricated using thin metallic films, as previously described. The heater 1504 was pulsed 40 times every second, with a pulse of 100 microsecond duration. Due to the decompression caused by the motion of the piston 1501, a flow of fluid from the heater 1504 towards the detector 1505 was always present, causing any bubbles generated by the heater 1504 to move towards the detector 1505. While the sample was above the BP pressure, the bubbles nucleated at the heater 1504 quickly to recombine with the liquid, disappearing before reaching the detector 1505. When the BP pressure was crossed, however, the bubbles nucleating by the heater 1504 reversed their behavior and started growing. The detector 1505 then was able to detect the growing bubbles.

Figure 16A:
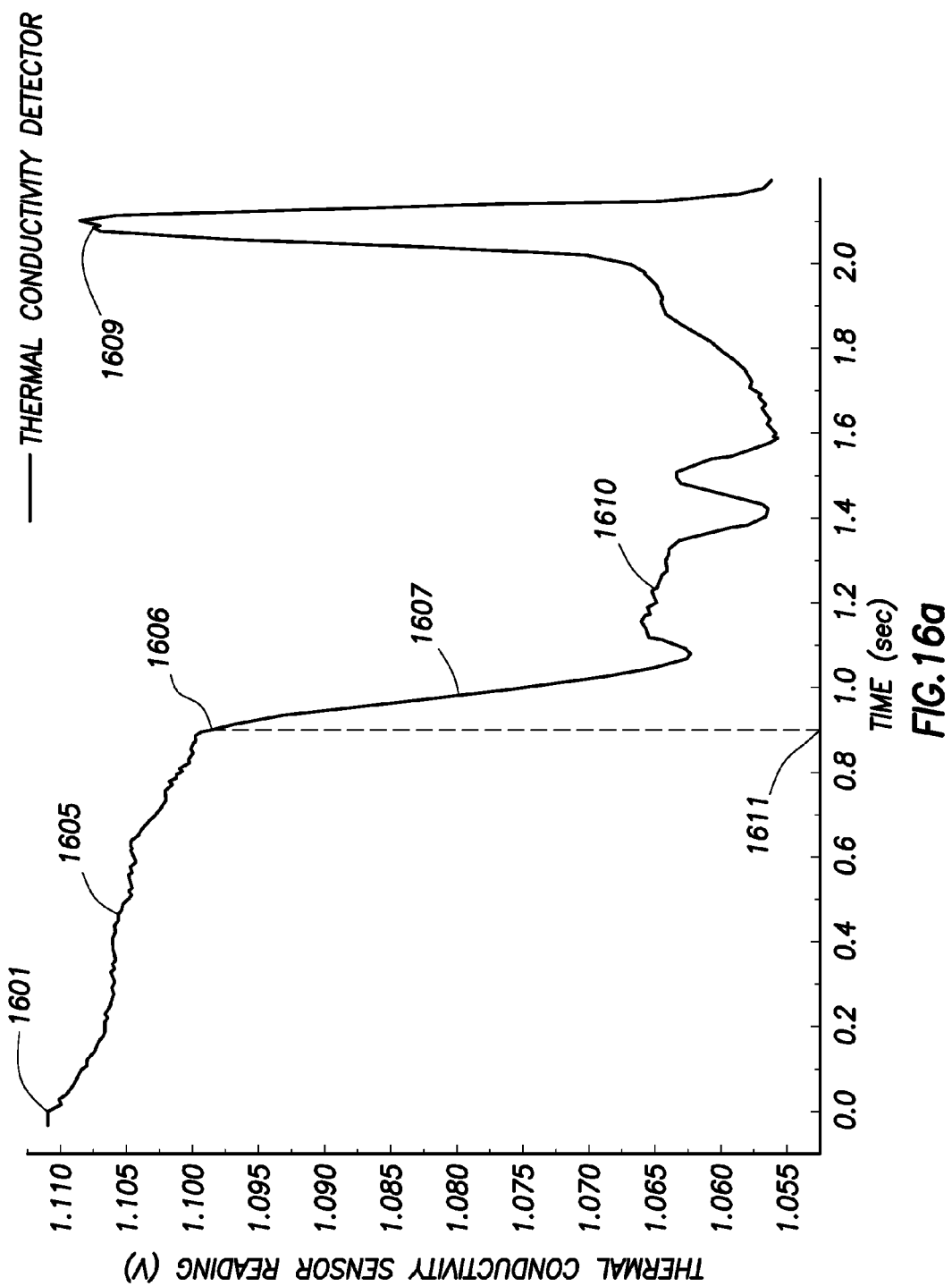

FIGS. 16a and 16b show exemplary data acquired during such an experiment. FIG. 16a shows the signal from the thermal conductivity detector 1505 during the sample decompression. The decompression began at 1601 on the graph. While in single-phase region (above the BP pressure) the detector 1505 read a high value, corresponding to high thermal-conductivity characteristic of the liquid phase. As soon as the BP pressure was reached, the detector 1505 output changed behavior abruptly at 1606 and started to decrease sharply at 1607 to a level at 1610 corresponding to low thermal conductivity characteristic of the gas. This abrupt change at 1606 in signal level was automatically detected by any suitable control software and the time at 1611 corresponding to the abrupt change of behavior was recorded, and corresponds to the time of crossing the BP pressure.

FIG. 16b shows the recording of the pressure gauge 1503 during the above experiment. In FIG. 16b, sample decompression was initiated at 1601, after which the pressure dropped abruptly after 1601, as sample volume was increased. The abrupt curve at 1602 corresponds to low compressibility characteristic of single-phase liquids. At 1603, the pressure behavior changed from varying rapidly to varying slowly at 1604, which corresponds to increased compressibility characteristic of the gas phase.

It is notable on the graphs of FIGS. 16a and 16b that the time of detection of the compressibility change at 1612 is later than the time of the detection of the first bubble at 1611. Without being bound by any operability theory, this is due to the condition of supersaturation in the sample fluid, wherein spontaneous nucleation (e.g., which is detected using the change in compressibility) occurs at pressures significantly lower than the actual bubble point pressure at 1615. In the case of this experiment, spontaneous nucleation occurred at a pressure of approximately 900 psi, or 50 psi below the actual bubble point pressure of the sample, as shown in FIG. 16b. The pressure corresponding to the detection of the first bubble at 1614 corresponds to 950 psi, which is the correct bubble point pressure of the sample.

This experiment shows that sample expansion experiments, which do not involve active nucleation, can lead to significant errors in the measurement of bubble point pressure, whereas the novel thermal nucleation and detection techniques of the exemplary embodiments, advantageously, result in very accurate measurements of the bubble point pressure and without errors due to sample supersaturation, and the like.

It will be apparent to those skilled in the art that various embodiments exemplified herein can be modified for a particular application, which may require a change in dimensions or arrangement of the exemplary embodiments. Thus, for example, the heater elements 106 can be made of metals other than titanium-platinum, e.g., aluminum, gold, nickel, chrome, pure titanium, pure platinum, polysilicon, and the like, and their thickness can range from about 1 nanometer to about 100 micrometers. The constriction created by the metal strips of the film of the metals, for example, can have a size of about 100 nanometers to about 1 millimeter. The amount of thermal energy injected in the heater 106, for example, can be about 0.01 milliJoules to about 10 Joules, and the length of the applied pulses, for example, can be about 1 microsecond to about 1 second.

All or a portion of the devices and subsystems of the exemplary embodiments can be conveniently implemented by the preparation of application-specific integrated circuits or by interconnecting an appropriate network of conventional component circuits, as will be appreciated by those skilled in the electrical art(s). Thus, the exemplary embodiments are not limited to any specific combination of hardware circuitry and/or software. In addition, one or more general purpose computer systems, microprocessors, digital signal processors, microcontrollers, and the like, can be employed and programmed according to the teachings of the exemplary embodiments of the present inventions, as will be appreciated by those skilled in the computer and software arts. Appropriate software can be readily prepared by programmers of ordinary skill based on the teachings of the exemplary embodiments, as will be appreciated by those skilled in the software art(s).

Thus, the exemplary embodiments describe and demonstrate a method, system and devices capable of measuring BP pressure of an oil-gas mixture, for example, by (i) nucleating bubbles thermally, (ii) detecting the bubbles (e.g., thermally as well) and monitoring their behavior, (iii) performing (i) and (ii) in a microfluidic system, and (iv) utilizing (i) and (ii) and providing the required pressure drop of the sample by using viscous drag, advantageously, without requiring any moving parts. The steps (i)-(iii) can be independent from each other.

There are several ways the above steps can be combined, for example, including:

Using (i) in order to nucleate bubbles regardless of what bubble detection technique is used subsequently, or how pressure is decreased in the sample from borehole pressure down to below BP pressure. Advantageously, this allows thermal nucleation to be retrofitted to existing BP pressure measurement setups, in order to replace existing nucleation means, e.g., ultrasonic actuators or mechanical impellers.

Using (i) and (ii) in order to nucleate bubbles and then detect them at the place of nucleation or any suitable place downstream therefrom. Advantageously, this provides much better measurement quality over the existing state-of-the-art systems, because the bubble position and time of nucleation can be controlled.

Using (i), (ii) and (iii) to take advantage of all the benefits of miniaturization, including much faster heating and cooling rates, small sample volume, confinement of the nucleated bubbles. This implementation leads to the most accurate BP pressure measurement, as the maximum amount of control is imposed. The pressure drop in the system can be controlled either mechanically, using, for example, pistons to vary the sample volume, or using other means such as (iv). Advantageously, this measurement scheme can be implemented either in the lab or downhole.

Using (i), (ii), (iii) and (iv) to provide a complete system for measuring bubble point pressure, downhole or on surface.

Although the exemplary embodiments are described in terms of oilfield applications, the exemplary embodiments can be employed with any other suitable applications, as will be appreciated by those skilled in the relevant art(s).

While the present inventions have been described in connection with a number of exemplary embodiments, and implementations, the present inventions are not so limited, but rather cover various modifications, and equivalent arrangements, which fall within the purview of the present claims.

What is claimed is:

1. An apparatus for nucleating bubbles in an oil-gas mixture, the apparatus comprising:
   a chamber configured to receive a sample comprising an oil-gas mixture; and
   a heater configured to heat the sample until at least one bubble is thermally nucleated in the chamber, wherein the heater comprises a metallic heating filament and wherein the chamber and the heater are included in a system or device and which includes a plurality of chambers interconnected by at least one capillary.

2. The apparatus of claim 1, wherein viscous drag caused by fluid flow through the interconnected chambers and the at least one capillary produces enough pressure drop of the sample for determining the BP pressure of the sample.

3. The apparatus of claim 1, further comprising means for determining the bubble point (BP) pressure of the sample.

4. The apparatus of claim 3, wherein the means for determining the bubble point (BP) pressure of the sample comprises at least two sensors placed at two distinct points of the apparatus.

5. The apparatus of claim 4, wherein the apparatus is configured to measure BP pressure of the oil-gas mixture downhole or on surface.

6. The apparatus of claim 1, wherein the system is provided with external means for modifying pressure of the sample.

7. The apparatus of claim 6, wherein the means for modifying pressure of the sample includes an externally actuated and controlled piston, a diaphragm or a system of bellows.

8. The apparatus of claim 7, wherein the modification of the sample pressure includes modifying the sample volume.

9. The apparatus of claim 1, wherein the chambers are micro-chambers.

10. The apparatus of claim 9, wherein the micro-chambers are part of a micro-fluidic apparatus.

11. The apparatus of claim 1, wherein the heater is a micro-heater.

12. The apparatus of claim 11, wherein the micro-heater is part of a micro-fluidic apparatus.

13. The apparatus of claim 1, further including a detection means for detecting the at least one thermally nucleated bubble.

14. The apparatus of claim 13, wherein detection of the at least one nucleated bubble is performed by optically monitoring a behavior thereof using an optical device.

15. The apparatus of claim 13, wherein the detection of the at least one nucleated bubble is performed using a thermal technique using a thermal means.

16. The apparatus of claim 15, wherein the thermal technique includes using the same heater as a thermal conductivity detector after the thermal nucleation of the bubble.

17. The apparatus of claim 15, wherein the thermal technique includes using a thermal conductivity detector that is separate from the heater and physically located in a path of travel of the bubble nucleated at the heater.

18. A micro-fluidic apparatus for nucleating bubbles in an oil-gas mixture, the micro-fluidic apparatus comprising:
    a micro-chamber configured to receive a sample comprising an oil-gas mixture;
    a micro-heater configured to heat the sample until at least one bubble is thermally nucleated in the micro-chamber, wherein the micro-heater comprises a metallic heating filament;
    a capillary in fluid communication with the micro-chamber, the capillary having an inlet for introducing the sample into the micro-chamber, and an outlet; and
    detection means for detecting the at least one nucleated bubble and monitoring the behavior thereof.

19. The micro-fluidic apparatus of claim 18, further comprising external means for modifying pressure of the sample operably connected to the micro-chamber.

20. The micro-fluidic apparatus of claim 18, wherein heating the sample until at least one bubble is thermally nucleated in the micro-chamber minimally affects the average temperature of the sample.

21. The micro-fluidic apparatus of claim 18, wherein detection means includes optically monitoring a behavior thereof.

22. The micro-fluidic apparatus of claim 18, wherein the micro-chamber and micro-heater are among a plurality of micro-chambers interconnected by a plurality of capillaries.

23. The micro-fluidic apparatus of claim 18, wherein detection means includes using a thermal technique.

24. The micro-fluidic apparatus of claim 23, wherein the thermal technique includes using the micro-heater as a thermal conductivity detector after the thermal nucleation of the bubble.

25. The micro-fluidic apparatus of claim 23, wherein the thermal technique includes using a thermal conductivity detector that is separate from the micro-heater, and physically located in a path of travel of the bubble nucleated at the heater.

26. The micro-fluidic apparatus of claim 18, further comprising means for determining the BP pressure of the sample.

27. The micro-fluidic apparatus of claim 26, wherein the means for determining the BP pressure of the sample comprises at least two sensors placed at two distinct points of the micro-fluidic apparatus.

28. The micro-fluidic apparatus of claim 26, wherein the means for determining the BP pressure of the sample is configured to measure BP pressure of the sample downhole or on surface.

* * * * *